United States Patent [19]
Matsunaga et al.

[11] Patent Number: 5,968,743
[45] Date of Patent: Oct. 19, 1999

[54] DNA SEQUENCING METHOD AND REAGENTS KIT

[75] Inventors: Hiroko Matsunaga, Kokubunji; Kazunori Okano, Shiki; Hideki Kambara, Hachioji, all of Japan

[73] Assignee: Hitachi, Ltd., Tokyo, Japan

[21] Appl. No.: 08/948,364

[22] Filed: Oct. 9, 1997

[30] Foreign Application Priority Data

Oct. 14, 1996 [JP] Japan .................................. 8-270564

[51] Int. Cl.⁶ .............................. C12Q 1/68; C12P 19/34
[52] U.S. Cl. ................................................ 435/6; 435/91.2
[58] Field of Search ........................ 435/6, 91.2; 935/77, 935/78; 536/22.1

[56] References Cited

FOREIGN PATENT DOCUMENTS

| 767240 | 4/1997 | European Pat. Off. |
|--------|--------|--------------------|
| 9613634 | 1/1996 | Japan . |

OTHER PUBLICATIONS

T. Maniatis et al, Molecular Cloning, Cold Spring Harbor Laboratory Press, 1989, Chapter 13, pp. 21–33.
T. Maniatis et al, Molecular Cloning, Cold Spring Harbor Laboratory Press, 1989, Chapter 13, pp. 14–20.
T. Maniatis et al, Molecular Cloning, Cold Spring Harbor Laboratory Press, 1989, Chapter 13, pp. 34–41.
Gene, 176, 1996, "Fragment Walking for long DNA sequencing by using a library as small as 16 primers", K. Okano et al, pp. 231–235.
T. Maniatis et al, Molecular Cloning, Cold Spring Harbor Laboratory Press, 1989, Chapter 5, pp. 62–63.
T. Maniatis et al, Molecular Cloning, Cold Spring Harbor Laboratory Press, 1989, Chapter 5 pp. 56–57.
Kazunori et al, Gene 176:231–235, 1996.

*Primary Examiner*—Eggerton A. Campbell
*Attorney, Agent, or Firm*—Fay, Sharpe, Beall, Fagan, Minnich & McKee

[57] ABSTRACT

The present invention provides a DNA sequencing method comprising: (1) a step of fragmentation of a sample DNA and amplifying each fragment to obtain a first DNA fragment; (2) a step of obtaining from the first DNA fragment a second DNA fragment substantially complementary to the sample DNA at least at the 3' terminus thereof; and (3) a step of performing an extension reaction of complementary strand, using the sample DNA as a template to produce a third DNA fragment containing a base sequence complementary to the second DNA fragment and having a size longer than that of the second DNA fragment, and using the third DNA fragment as a template for sequencing of the sample DNA. DNA sequencing can be proceeded efficiently with extremely low redundancy.

20 Claims, 13 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "synthetic DNA"

(xi) SEQUENCE DESCRIPTION: SEQ ID NO:1:

TGTAAAACGA CGGCCAGT                                                18

(2) INFORMATION FOR SEQ ID NO:2:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "synthetic DNA"

(xi) SEQUENCE DESCRIPTION: SEQ ID NO:2:

ACAGGAAACA GCTATGAC                                                18

DNA SEQUENCING METHOD AND REAGENTS KIT

BACKGROUND OF THE INVENTION

1. Field of the Invention

The present invention relates to a method for sample preparation efficiently provided for a DNA sequencing process, which basic technology utilizes an enzymatic extension reaction of complementary strand. The present invention also relates to a reagents kit for use in the DNA sequencing process.

2. Description of the Related Art

Focusing on human genome analyses, a high throughput and highly efficient DNA sequencing technology is required. DNA sequencing starts from the preparation of DNA library which covers all DNAs, by making clones having a length of 10 Kbp to 100 Kbp from the DNAs present in a gene. DNA sequencing of clones thus produced has been conventionally relied upon and roughly classified into three techniques, i.e., shotgun, primer-walking and nested-deletion techniques.

The shotgun technique involves digesting a sample DNA at random by sonication, preparing DNA fragments by subcloning and sequencing each fragment, whereby overlaps of the sequenced fragments are used to determine the full-length base sequence. Details of the shotgun technique are described in, e.g., T. Maniatis et al.: Molecular Cloning, Cold Spring Harbor Laboratory Press, 13, 21–33 (1989).

According to the primer-walking technique, sequences of DNA fragments to be sequenced are sequentially determined one by one from the terminus thereof. That is, in the primer-walking technique, one end of a sample DNA is first sequenced. Next, sequences for a primer contiguous to the following region are selected from the thus determined base sequences. DNA sequencing again starts from the selected sequences. Technical details on the primer walking technique are described in, e.g., T. Maniatis et al.: Molecular Cloning, Cold Spring Harbor Laboratory Press, 13, 14–20 (1989).

In the nested-deletion technique, fragments from a sample DNA are subjected to enzymatic digestion to prepare fragments with slightly different sizes. After one end of these fragments is trued up, the fragments are sequenced from another end in the order of a longer length. Details of the nested-deletion technique are found in, e.g., T. Maniatis et al.: Molecular Cloning, Cold Spring Harbor Laboratory Press, 13, 34–41 (1989).

In the shotgun method described above, what portion of the sample DNA corresponds to DNA extracted by subclone is unknown until the full-length base sequence is determined. For this reason, it is necessary to analyze the DNA length longer by 10 to 20 times than the length of a DNA strand to be actually sequenced. Therefore, intensive time and labors are required, resulting in serious obstacles. Turning to the primer walking technique mentioned above, this technique provides more efficient DNA sequencing but involves disadvantages, since successive operations for sequencing is time-consuming and a primer must be prepared every time when sequencing is done.

According to the nested-deletion technique mentioned above, new information on a sequence corresponding to the difference in length between fragments is always obtained. The nested-deletion technique is thus efficient, because DNA sequencing is performed sequentially from one end, as in the primer-walking method. Furthermore, the thus prepared DNA fragment is inserted into a plasmid for subcloning and the subclone is then sequenced. Accordingly, a priming site is obtained from the base sequence of plasmid, meaning that there is no need to prepare a primer for DNA sequencing every time. In view of these characteristics of the nested-deletion method, it appears that this method may overcome the problems encountered in the shotgun and primer walking techniques. From a practical viewpoint, however, time-consuming operations for selecting and arranging samples convenient for DNA sequencing are required after all. This is a key how to meet the requirement. In addition, purification by subcloning that is commonly performed in the shotgun and nested-deletion methods is such a complicated operation that is a serious problem to be solved.

In order to solve the problems of complicated operations required for DNA sequencing as recognized in the three techniques hitherto applied, various attempts have been made. In particular, direct sequencing of DNA fragments in a mixture obtained from a sample DNA digested with a restriction enzyme is a promising method. This technique is called a fragment-walking method, which is briefly explained below and a more detailed explanation is found in, e.g., K. Okano et al., Gene, 176: 231–235 (1996), "Fragment walking for large DNA sequencing by using a library as small as 16 primers". A sample DNA is digested with a restriction enzyme. Thereafter an oligomer having a known sequence is ligated with the DNA fragment at the terminus thereof through a ligation reaction to recognize each DNA fragment in the fragments mixture. Sequencing reaction is then conducted using a set of primers which can discriminate a complementary base sequence to at least a part of the ligated oligomer and the restriction enzyme recognition sequence, and an unknown one-base to four-bases sequence adjacent to the recognition sequence. The primer set includes, for example, 16 combinations of all possible bases in the case of an unknown base sequence having variable two base sequence. Where a small number of DNA fragments are contained in a DNA fragment mixture and one DNA fragment forms a complete base pairing with one primer, the base sequence of each DNA fragment can be determined from the mixture, respectively, using the set of primers described above. Where one primer hybridizes to at least two DNA fragments, the above procedure is performed, e.g., after separation of DNA fragments depending upon size. After the base sequence of each DNA fragment has been determined, the base sequences of the respective DNA fragments are reconstructed to obtain the overall base sequence. In order to obtain the overall base sequence, there is employed a method in which fragments are walked over to determine the DNA sequence of the overlapping portion, using as a template for sequencing each fragment and a full-length intact sample DNA before a digestion reaction with any restriction enzyme. Alternatively, there is employed another method in the number of restriction enzymes used initially is increased and the overall DNA sequence is determined by making use of the overlapping base sequence between the fragments.

As explained above, those conventional techniques are all somehow disadvantageous. That is, the shotgun technique requires repeated reading of the same base sequence and is thus inefficient due to high redundancy. For reducing redundancy, the primer-walking technique and the nested-deletion technique have been proposed. However, the primer-walking technique involves disadvantages that prior to DNA sequencing, primers must be synthesized every time or it is necessary to prepare a library including a huge number of primers and it takes much time for DNA sequencing in a series. Turning to the nested-deletion technique, this method is disadvantageous in that a sample convenient for DNA sequencing is prepared only with difficulty. Additional problems encountered with the shotgun and nested-deletion techniques are seen in much time and labors required for cloning using a culture step that is automated also only with difficulty. Contrary to the two techniques above, the fragment-walking method is advantageous in that this technique does not require such cloning and provides low redundancy but is reduced but where the digested fragments have long DNA sequences, difficulties occur in their connection.

SUMMARY OF THE INVENTION

An object of the present invention is to provide a method for DNA sequencing of a sample DNA which involves sample preparation for the nested-deletion technique from fragments prepared by the fragment-walking method, followed by sequential DNA sequencing, whereby difficulties in fragment connection in the fragment-walking technique and difficulties in sample preparation and complicated operations for subcloning in the nested-deletion method can be eliminated.

Another object of the present invention is to provide a reagents kit for use in the DNA sequencing method.

(1) According to DNA sequencing method (A) as a first aspect of the present invention, the sequencing method (A) comprises:

(A1) a step of digesting a sample DNA with a restriction enzyme(s) to obtain a DNA fragment(s);

(A2) a step of introducing an oligomer having a known base sequence into the DNA fragments at the 3' termini thereof;

(A3) a step of performing an extension reaction of complementary strand, using each labeled primer (with, e.g., a fluorophore label) comprising a first sequence complementary to at least a part of the oligomer, a second sequence complementary to the restriction enzyme recognition sequence and a third arbitrary two base sequence from possible combinations of all four bases A, C, G and T (hereinafter an unlabeled primer having this base sequence is referred to as a selective primer), by using, as a template, the oligomer-introduced DNA fragment to determine the two base sequences adjacent to the restriction enzyme recognition sequence of the oligomer-introduced DNA fragment;

(A4) a first amplification step for amplifying each DNA fragment based on the sequencing information determined at step (A3), using the oligomer-introduced DNA fragment as a template;

(A5) a step of degrading one strand of the amplified product located near one of the 5' termini and near both strands of the 3' termini to obtain a part of single strand located near the 5' terminus; and, (A6) a second amplification step for performing amplification of each DNA fragment, using as a template an intact sample DNA prior to restriction enzyme digestion by using, as primers, an oligomer having a part of sequences of the sample DNA and a part of single stranded DNA located near the 5' terminus thereof, which has been purified at step (A5), to determine the base sequence of the product.

The above method (A) is further characterized in that at step (A2) for introducing the oligomer with a known base sequence, or adding deoxyribonucleotide oligomer using terminal deoxynucleotidyl transferase (hereinafter abbreviated as TdT); at step (A4), one out of the two primers is phosphorylated at the 5' terminus thereof; and at step (A5), λ-exonuclease which is a 5'→3' exonuclease is employed to degrade the vicinity to the 5' terminus and, for degradation of the vicinities to the 3' termini, there is employed any one of Klenow fragment, T4 DNA polymerase, exonuclease III and BAL31 exonuclease which are enzymes having a 3'→5' exonuclease activity.

(2) According to DNA sequencing method (B) as a second aspect of the present invention, step (A6) in method (A) is modified to the following step (B6). That is, steps (B1) through (B5) are the same as steps (A1) through (A5), respectively, and (B6) comprises:

(B6) a second amplification step of performing amplification of each DNA fragment, using as templates a part of single stranded DNA located near the 5' terminus thereof, which has been purified at step (B5), namely, step (A5) and an intact sample DNA prior to restriction enzyme digestion by using an oligomer having a part of sequences of the sample DNA and one selective primer having the same sequence as a part of single stranded DNA located near the 5' terminus thereof, to determine the base sequence of the product.

The above method (B) is further characterized in that at step (B2), i.e., step (A2) for introducing the oligomer having a known base sequence, or adding deoxyribonucleotide oligomer using TdT; at step (B4), i.e., step (A4), one out of the two primers is phosphorylated at the 5' terminus thereof; and at step (B5), i.e., step (A5), λ-exonuclease which is a 5'→3' exonuclease is employed to degrade the vicinity to the 5' terminus and, for degradation of the vicinities to the 3' termini, there is employed any one of Klenow fragment, T4 DNA polymerase, exonuclease III and BAL31 exonuclease which are enzymes having a 3'→5' exonuclease activity.

(3) As a third aspect (C) of the present invention, there is provided a reagents kit (C) for DNA sequencing comprising:

a restriction enzyme(s) for digesting DNA strands;

an oligomer having a known base sequence; a reagent kit for introducing the oligomer having a known base sequence into DNA at the terminus thereof comprising at least a ligase or TdT;

a set of 16 selective primers for extension reaction of complementary strand; and, enzymes having a 5'→3' exonuclease activity and having a 3'→5' exonuclease activity.

(4) In a fourth aspect (D) of the present invention for DNA sequencing, steps (A5) and (A6) of the method (A) are modified to the following steps (D5) and (D6). That is, steps (D1) through (D4) are the same as steps (A1) through (A4), respectively. Thus, the method (D) for DNA sequencing further comprises:

(D5) a step of degrading the vicinities to the 3' termini of the amplified fragment to obtain a part of single stranded DNA located near the 5' terminus thereof; and, (D6) a second amplification step for amplifying each DNA fragment, using as a template an intact sample DNA prior to restriction enzyme digestion, only one strand of which DNA has been purified, by using, as primers, an oligomer having a part of sequences of the sample DNA and a part of single stranded DNA located near the 5' terminus thereof, which has been purified at step (D5), to determine the base sequence of the product.

The above method (D) is further characterized in that at step (D2), i.e., step (A2) for introducing the oligomer having a known base sequence, or adding deoxyribonucleotide oligomer using TdT; and at step (D5), any one of Klenow fragment, T4 DNA polymerase, exonuclease III and BAL31 exonuclease which are enzymes having a 3'→5' exonuclease activity is employed for degradation of the vicinities to the 3' termini.

(5) In a fifth aspect (E) of the present invention for DNA sequencing, step (D6) of the method (D) is modified to the following step (E6). That is, steps (E1) through (E5) are the same as steps (D1) through (D5), respectively. Thus, the method (E) for DNA sequencing further comprises:

(E6) a second amplification step for amplifying each DNA fragment, using as templates a part of single stranded DNA located near the 5' terminus thereof, which has been purified at step (E5), namely, step (D5) and an intact sample DNA prior to restriction enzyme digestion, only one strand of which DNA has been purified, by using, as primers, an oligomer having a part of sequences of the sample DNA and one selective primer having the same sequence as a part of single stranded DNA located near the 5' terminus thereof, which has been purified at step (E5), namely, step (D5), to determine the base sequence of the product.

The above method (E) is further characterized in that at step (E2), i.e., step (A2) for introducing the oligomer having a known base sequence, or adding deoxyribonucleotide oligomer using TdT; and at step (E5), i.e., step (D5), any one of exonuclease III and BAL31 exonuclease which are 3'→5' exonuclease enzymes is employed for degradation of the vicinities to the 3' termini.

(6) As a sixth aspect (F) of the present invention, there is further provided a reagents kit (F) for DNA sequencing comprising:

a restriction enzyme(s) for digesting DNA strands;

an oligomer having a known base sequence;

a reagent for introducing the oligomer having a known base sequence into DNA at the terminus thereof comprising at least a ligase or TdT;

a set of 16 selective primers for extension reaction of complementary strand; and, a 3'→5' exonuclease.

(7) In a seventh aspect (G) of the present invention for DNA sequencing, steps (A5) and (A6) of the method (A) are modified to the following steps (G5) to (G7). That is, steps (G1) through (G4) are the same as steps (A1) through (A4), respectively. Thus, the method (G) for DNA sequencing further comprises:

(G5) a step of degrading the vicinity to the 5' terminus of the amplified fragment;

(G6) a step of degrading a part of single stranded DNA; and, (G7) a second amplification step for amplifying each DNA fragment, using as a template an intact sample DNA prior to restriction enzyme digestion by using, as primers, an oligomer having a part of sequences of the sample DNA and a part of single strand located near one of the 5' terminus, which has been purified at steps (G5) and (G6), to determine the base sequence of the product.

The above method (G) is further characterized in that at step (G2), i.e., step (A2) for introducing the oligomer having a known base sequence, or adding deoxyribonucleotide oligomer using TdT; at step (G4), i.e., step (A4), one out of the two primers is phosphorylated at the 5' terminus thereof; at step (G5), λ exonuclease which is a 5'→3' exonuclease is employed for degradation of the vicinity to the 5' terminus; and at step (G6) for the degradation of single stranded DNA, S nuclease or Mung Bean nuclease is employed.

(8) In an eighth aspect (H) of the present invention for DNA sequencing, step (G7) of the method (G) is modified to the following step (H7). That is, steps (H1) through (H6) are the same as steps (G1) through (G6), respectively. Thus, the method (H) for DNA sequencing further comprises:

(H7) a second amplification step for amplifying each DNA fragment, using as templates a part of single strand located near one of the 5' terminus thereof, which has been purified at step (H5), i.e., step (G5) and step (H6), i.e., step (G6), and an intact sample DNA prior to restriction enzyme digestion by using, as primers, an oligomer having a part of sequences of the sample DNA and one selective primer having the same sequence as a part of single strand located near one of the 5' terminus thereof, to determine the base sequence of the product.

The above method (H) is further characterized in that at step (H2), i.e., step (A2), for introducing the oligomer having a known base sequence, or adding deoxyribonucleotide oligomer using TdT; at step (H4), i.e., step (A4), one out of the two primers is phosphorylated at the 5' terminus thereof; at step (H5), i.e., step (G5), λ exonuclease which is a 5'→3' exonuclease is employed for degradation of the vicinity to the 5' terminus; and at step (H6), i.e., step (G6) for the degradation of single stranded DNA, S nuclease or Mung Bean nuclease is employed.

(9) As a ninth aspect (I) of the present invention, there is further provided a reagents kit (I) for DNA sequencing comprising:

a restriction enzyme(s) for digesting DNA strands;

an oligomer having a known base sequence; a reagent for introducing the oligomer having a known base sequence into DNA at the terminus thereof comprising at least a ligase or TdT;

a set of 16 selective primers for extension reaction of complementary strand;

a 5'→13' exonuclease; and, an enzyme(s) for digesting single stranded DNA.

(10) In a tenth aspect (J) of the present invention for DNA sequencing, the second amplification step which corresponds to step (A6) in the method (A), step (D6) in the method (D) and step (G7) in the method (G) is modified to the following step (J1). That is, the method (J) is modified to include:

(J1) a second amplification step for amplifying each DNA fragment, using as a template an intact sample DNA prior to restriction enzyme digestion by using a part of single stranded DNA located near the 5' terminus thereof, which has been prepared from sample DNA, and a random primer (an oligomer having a random base sequence), to determine the base sequence of the product.

In an eleventh aspect (K) of the present invention for DNA sequencing, the second amplification step which corresponds to step (B6) in the method (B), step (E6) in the method (E) and step (H7) in the method (H) is modified to the following step (K1). That is, the method (K) is modified to include:

(K1) a second amplification step for amplifying each DNA fragment, using, as templates, a part of single stranded DNA located near the 5' terminus thereof, which has been prepared from sample DNA, and an intact sample DNA prior to restriction enzyme digestion by using a random primer (an oligomer having a random base sequence) and one selective primer having the same sequence as a part of single stranded DNA located near the 5' terminus thereof, to determine the base sequence of the product.

In the present invention, a sample DNA is fragmented with a restriction enzyme and the resulting fragment is amplified by polymerase chain reaction (hereafter abbreviated as PCR). The thus amplified fragment is degraded with an enzyme and only one strand of a part of double stranded DNA located near the 5' terminus thereof is recovered, in which the fragment is complementary to one of double strands of the sample DNA before the fragmentation. This complementary nature is utilized in the present invention. After a part of the single stranded DNA located near the 5' terminus thereof hybridizes to one strand of the intact sample DNA before digestion with a restriction enzyme, an extension reaction can be performed in the 3'-terminal direction using this hybrid DNA as a template. Furthermore, the oligomer having a part of the base sequence of the intact sample DNA before enzymatic digestion is complementary to the extension product of a part of single stranded DNA located near the 5' terminus of the DNA fragment and using the extension product as a template, an extension reaction can be carried out. Therefore, using as PCR primers single stranded DNA located near the 5' terminus of the DNA fragment and an oligomer having the same sequence as a part of sample DNA before enzymatic digestion or an oligomer having a random base sequence (random oligomer), the portion between the two primers can be amplified by PCR, as in steps (A6), (D6), (G7) and (J1). Likewise, after a part of the single stranded DNA located near the 5' terminus thereof hybridizes to one strand of the intact sample DNA before digestion with a restriction enzyme, an extension reaction can be performed in the 3' terminal direction using this hybrid DNA as a template. Thus, as in steps (B6), (E6), (H7) and (K1), using as templates the extension reaction product and intact sample DNA before enzymatic digestion and by using an oligomer having the same sequence as a part of single stranded DNA located near the 5' terminus of the DNA fragment and an oligomer having the same sequence as a part of sequences of the intact sample DNA before enzymatic digestion or a random primer (an oligomer having a random base sequence), the portion between the two primers can be amplified by PCR.

In the products obtained by the second amplification step using a template(s) and a primer(s), one terminus is all located at the same site of the intact sample DNA before enzymatic digestion (the position having the same base sequence as the oligomer) and another terminus is determined at the digestion site of a sample DNA with a restriction enzyme. Thus, the products of the same number as that of the DNA fragments after digestion with a restriction enzyme but having different sizes are produced so that a library for nested-deletion can be prepared.

According to the present invention, the two base sequence contiguous to the restriction enzyme recognition sequence of the fragment obtained by digestion of a sample DNA with a restriction enzyme is sequenced. Based on the thus obtained sequencing information, the fragment is amplified by PCR. Therefore, using a part of single stranded DNA located near one of the 5' terminus of the amplified fragment and an intact sample DNA before enzymatic digestion, second amplification can be performed by PCR to prepare a sample library for nested-deletion. Thus, DNA sequencing can be proceeded more efficiently with much lower redundancy than in the shotgun technique. Moreover, a sample DNA of a long size can be sequenced with only 16 primer sets prepared in advance, which makes it unnecessary to synthesize primers every time required for DNA sequencing by the primer-walking technique. Furthermore, a sample DNA is prepared by PCR amplification using the fragment obtained by digestion with a restriction enzyme so that a uniform library can be prepared. In addition, the present invention enables to give overlap information for sure on each fragment, which makes it easy to connect the sequenced fragments. In the present invention, subcloning is not required but the reactions are all carried out in vitro, thus enabling to sequence a sample DNA having a long base sequence.

The present invention is briefly explained with reference to FIG. 4. Sample DNA 151 is digested with a restriction enzyme. The resulting DNA fragment (fragment-1) is amplified using a selective primer set in 16 combinations and to obtain DNA 152 (fragment-2) located near the 5' terminus of one strand of each fragment through degradation with λ-exonuclease and Klenow fragment. Using the fragment-2 and sample DNA 151, PCR is performed to obtain DNA fragment 158 (fragment-3) containing the complementary base sequence to and longer than the fragment-2. The start point of fragment 158 is common but the end point differs depending upon restriction enzyme recognition sequences. By DNA sequencing starting from the restriction enzyme recognition sequence, DNA sequencing of sample DNA 151 can be performed efficiently over the full length.

DESCRIPTION OF THE PREFERRED EMBODIMENTS

The present invention will be described below in detail, with reference to embodiments and drawings.

EXAMPLE 1

Figure 1:
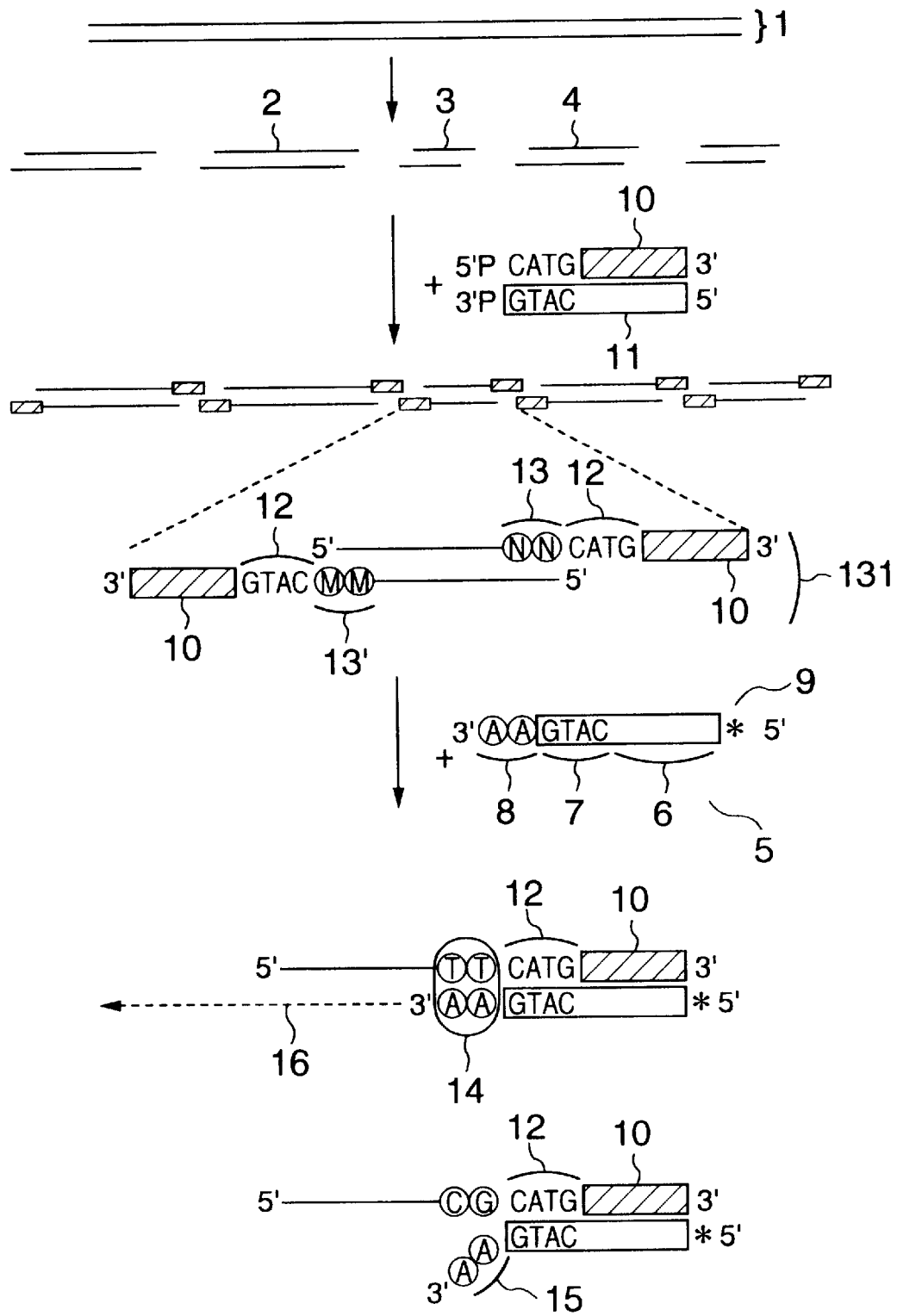
FIG. 1 is to explain, in an embodiment of the present invention, the steps of digesting a sample DNA with restriction enzymes and determining the two base sequence contiguous to the restriction enzyme recognition sequence of each fragment.

FIG. 1 shows the procedures in Example 1 of the present invention for explaining the steps of fragmentation of a sample DNA with restriction enzymes and then determining the sequence of two bases located next to the restriction enzyme recognition sequence of each fragment. As a sample DNA, there is employed about 8.9 kbs human genome DNA inserted into a plasmid.

Amplification of Sample DNA

Where the amount of sample DNA is insufficient for DNA sequencing, the sample DNA is amplified by PCR according to the following procedures. The following two primers, each having a base sequence complementary to the sample DNA-inserted plasmid, were employed.

```
Primer (1) having SEQ ID NO. 1:
5' - TGTAAAACGACGGCCAGT - 3'

Primer (2) having SEQ ID NO. 2:
5' - ACAGGAAACAGCTATGAC - 3'
```

A sample DNA inserted into a plasmid using two primers is subjected to PCR amplification, using thermo-stable polymerase Ex Taq (trademark, made by Takara Shuzo). The amplified sample DNA is subjected to 1% agarose gel electrophoresis followed by fractionation to remove the unreacted primers and dATP, dCTP, dGTP and dTTP. Thus, the PCR product of 8.9 kbs showing a single band is electrophoretically obtained in a high purity. Hereinafter this linear human genome DNA is called the PCR product, which is made sample DNA 1.

Fragmentation of Sample DNA

The sample DNA is digested with a restriction enzyme to produce DNA fragments. In this embodiment, restriction enzyme Hsp92II is used. Restriction enzymes such as HhaI, MboI, AluI, etc. may also be employed for digesting sample DNA 1 but not limited only to Hsp92II. In FIG. 1, numerals 2, 3 and 4 denote DNA fragments produced by digesting the sample DNA with a restriction enzyme. After the sample DNA is completely digested with Hsp92II at 37° C. for an hour, concentration and purification by ethanol precipitation were carried out thereby to inactivate and remove the restriction enzyme. Thereafter the reaction solution is all used to introduce a known base sequence, in accordance with the procedures for addition of an oligomer to the DNA fragment at the 3' terminus thereof, which will be described hereinafter.

Preparation of selective primer

A primer set called selective primer is prepared. The selective primer is used for the subsequent reaction. In FIG. 1, numeral 5 denotes a fluorophore labeled selective primer and numeral 9 denotes a fluorophore label. This primer comprises base sequence 6 complementary to at least a part of oligomer inserted into the digested DNA, base sequence 7 complementary to the recognition sequence of the restriction enzyme used to digest the sample DNA, and base sequence 8 of arbitrary two base sequence selected from four bases of A, C, G and T. As the fluorophore labeled selective primer there are 16 kinds resulting in all possible combinations of arbitrary two bases.

Introduction of Oligomer Having a Known Base Sequence into Both Termini of DNA Fragment There are two methods for introducing an oligomer having a known base sequence into the termini of DNA fragment. One method comprises ligating an oligomer having a known base sequence with a DNA fragment, as described in T. Maniatis et al., Molecular Cloning, Cold Spring Harbor Laboratory Press, 5, 62–63 (1989). In double strands of an oligomer for ligation (hereinafter referred to as adaptor), the 3' terminus of the adaptor contiguous to the 5' terminus of DNA fragment is phosphorylated. Likewise, the 5' terminus of the adaptor contiguous to the 3' terminus of the DNA fragment is also phosphorylated. The phosphorylation is performed to prevent adapters from ligating with each other. In order to prevent DNA fragments from ligation with each other, phosphates at the 5' termini of each fragment are removed with an alkaline phosphatase (CIAP). Another method comprises adding dATP (2'-deoxyadenosine 5'-triphosphate) or dUTP (2'-deoxyuridine 5'-triphosphate) to the 3' terminus of DNA fragment, see, e.g., T. Maniatis et al., Molecular Cloning, Cold Spring Harbor Laboratory Press, 5, 56–57 (1989). In Example 1, the former method is used, since the former is more stable in subsequent reactions than the latter method. In FIG. 1, numerals 10 and 11 denote adapters used in Example 1. The adaptor 11 has a protruding cohesive 3' terminus to ligate with the digested DNA fragment with Hsp92II. This adaptor and the concentrated and purified DNA fragment through ethanol precipitation were reacted at 15° C. overnight using T4 DNA ligase to ligate with each other. After the ligation, only strand 10 is actually ligated with the DNA fragment through a phosphodiester bond.

Sequencing of Two Bases Contiguous to the Restriction Enzyme Recognition Sequence of each DNA Fragment DNA fragment 131, its two strands introduced with the oligomers having known sequences, contains adaptor base sequences 10 and restriction enzyme recognition sequences 12 introduced at the termini, and parts 13, 13 ' of base sequences for selection. The parts of base sequences for selection are two bases, which sequences are discriminated by fluorophore labeled selective primer. In the following explanation, letters M and N designate any one of A, T, G and C; letter m designates a complementary base to base M and letter n designates a complementary base to base N. The part of base sequences for selection is composed of 1 to 4 bases, preferably 1 to 3 bases, more preferably 2 bases.

The DNA fragment produced by digesting a sample DNA is a mixture of a plurality of DNA fragments in kind. For selectively sequencing a desired DNA fragment alone, a fluorophore labeled selective primer is employed. As described above, arbitrary base sequences of the fluorophore labeled selective primer are 16 combinations in total. The sequence 6 complementary to the adaptor of fluorophore labeled selective primer and the sequence 7 complementary to the restriction enzyme recognition sequence can form complete pairing with the adaptor base sequence 10 and restriction enzyme recognition sequence 12 of all DNA fragments. As shown by numeral 14 in FIG. 1, the fluorophore labeled selective primer contains arbitrary two base sequences at the 3' terminus and only in the case of complete base pairing between DNA fragment and the two base sequences, complementary strand 16 can be formed. In the case of incomplete base pairing between the 3' terminal two bases of selective primer and DNA fragment as seen in numeral 15, no extension reaction proceeds. Utilizing this behavior, only the DNA fragment of complete pairing with each of 16 fluorophore labeled selective primers is selected from the mixture of DNA fragments. Thus, the two base sequences contiguous to the restriction enzyme recognition sequence of the DNA fragment are determined.

Figure 2:
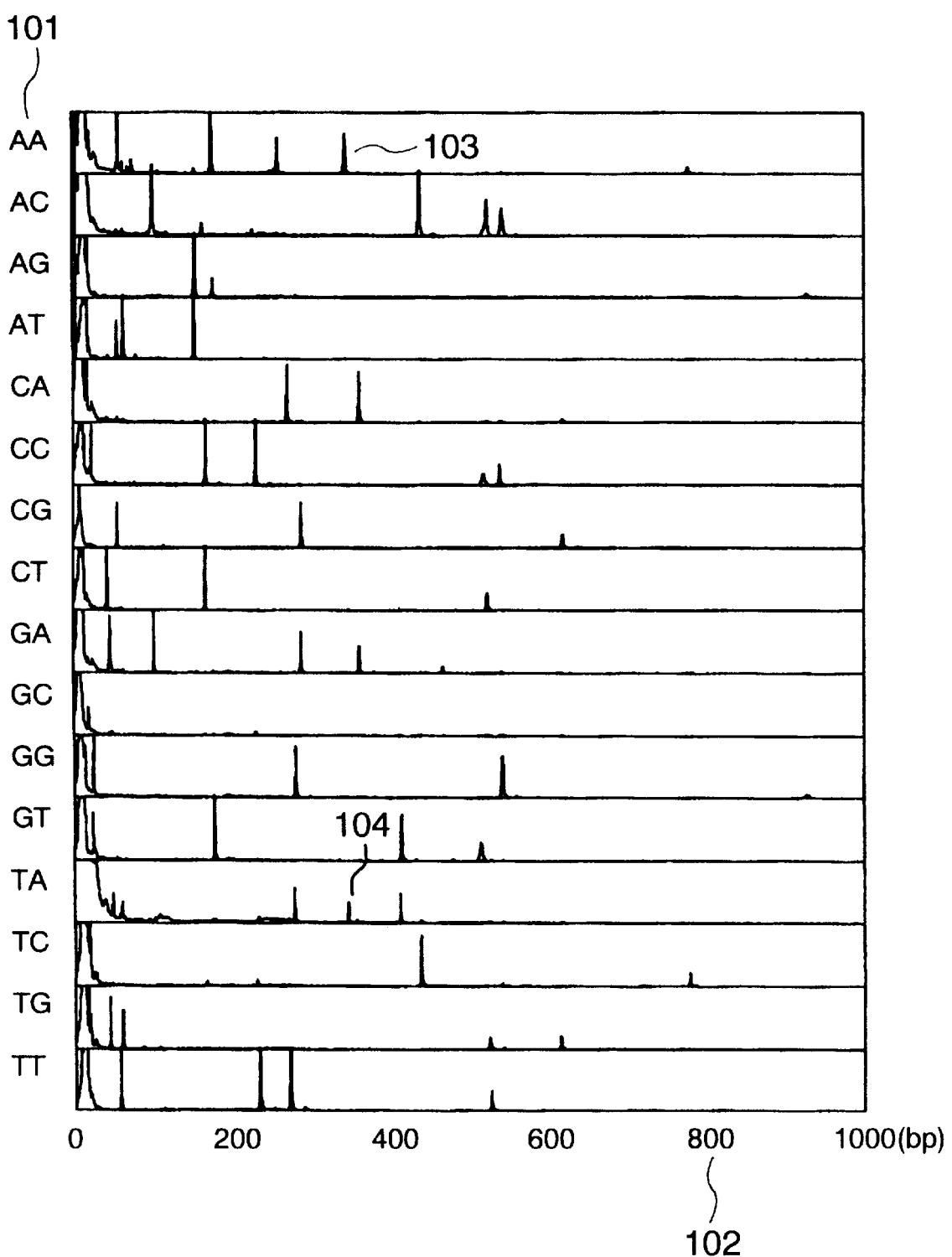
FIG. 2 shows gel electropherograms of the extension reaction products of complementary strands of DNA fragments obtained using selective primers of 16 combinations in an embodiment of the present invention.

In practice, DNA sequencing is carried out by the following procedures. After one fluorophore labeled selective primer, dATP, dCTP, dGTP, dTTP and thermostable DNA polymerase were added to the mixture of DNA fragments, the reaction of 5 cycles is carried out. A similar reaction is conducted with all other fluorophore labeled selective primers. Thereafter, the reaction product is analyzed by electrophoresis. FIG. 2 shows gel electropherograms of the extension reaction products of complementary strand of each DNA fragment obtained using 16 selective primers. In FIG. 2, the longitudinal axis 101 denotes 3'-terminal two base sequences of each selective primer and the traverse axis 102 indicates a base length. FIG. 2 gives the length of each fragment contained in the mixture of DNA fragments and information of the two base sequences contiguous to the restriction enzyme recognition sequences at the termini. As is seen from FIG. 2, for example, the peak 103 detected when using a fluorophore labeled selective primer having AA at the 3' terminus indicates that fragment TT of two base sequences contiguous to the restriction enzyme recognition sequence is present in the mixture. The peak 104 detected at the same position of the peak for AA means complementary base sequences to the two base sequences for anti-sense strand of a fragment with a base sequence of TT at the terminus of one strand of a DNA fragment. Thus, the two base sequences of two strands of each DNA fragment contained in the mixture of DNA fragments can be determined.

PCR Amplification of each DNA Fragment in the Mixture of DNA Fragments

Figure 3:
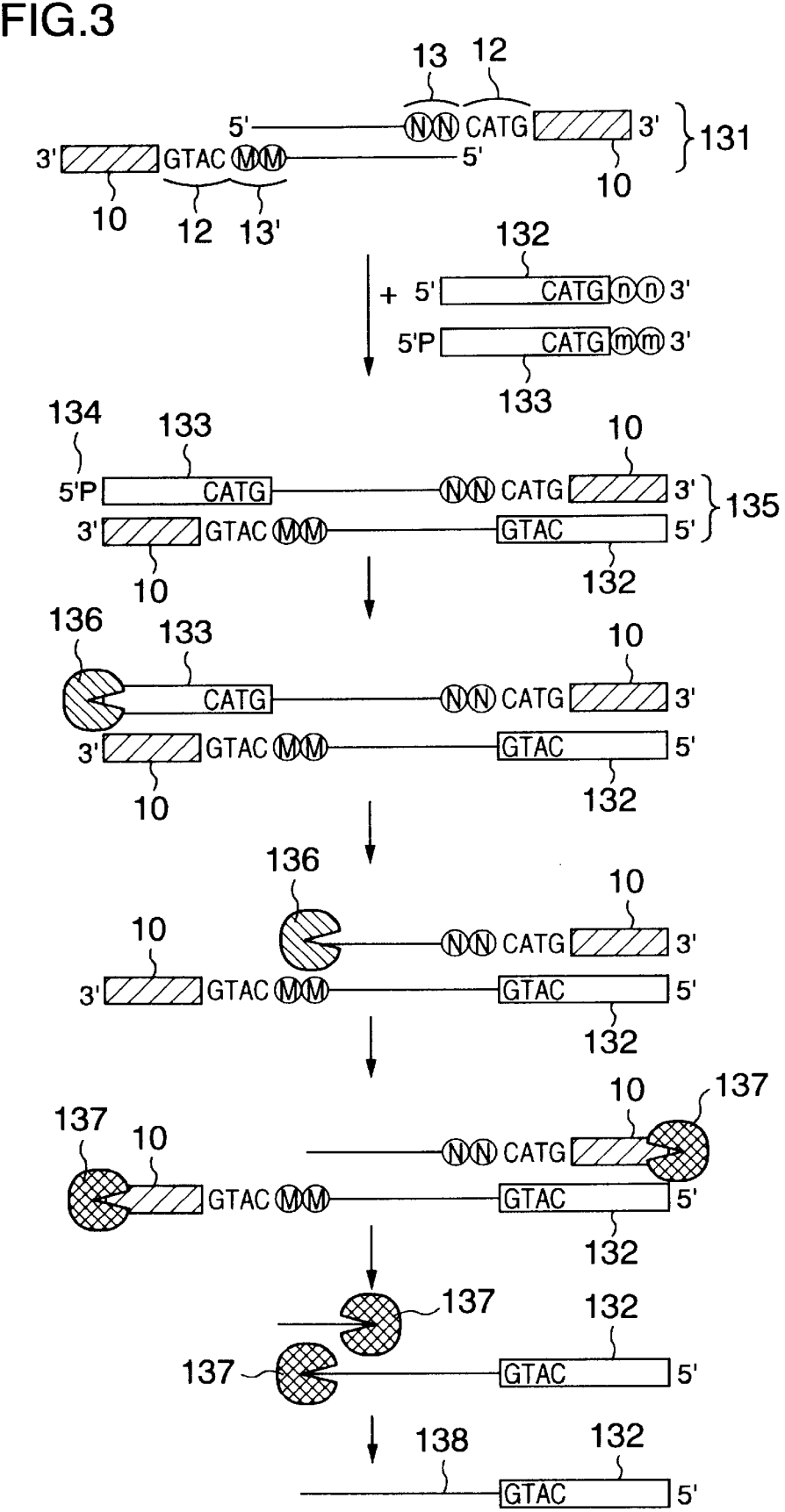
FIG. 3 is to explain, in an embodiment of the present invention, the steps of preparing a sample for nested-deletion library using enzymes having a 5'3' exonuclease activity and a 3'→5' exonuclease activity.

FIG. 3 is to explain the steps of preparing a sample for nested-deletion library using enzymes having a 5'→3' exonuclease activity and a 3'→5' exonuclease activity. Based on the sequencing information on the terminal two bases determined above, one DNA fragment selected from the mixture is amplified by PCR, using a pair of selective primers for each fragment. In FIG. 3, numeral 131 denotes a template DNA fragment. At this stage, one primer 133 out of paired two primers 132 and 133 used for the PCR reaction is modified and phosphorylated at the 5' terminus thereof. This modification serves to specific degradation of the phosphorylated 5' terminus 134 in FIG. 3, when one of the 5' terminus of the amplified DNA fragment is subsequently degraded. The DNA fragment amplified by PCR is purified and concentrated on a column QIA Quick Column (tradename, made by QUIAGEN Inc.) to remove the unreacted primers and dATP, dCTP, dGTP and dTTP. Hereinafter, the purified products are called PCR products of DNA fragments, which are made sample DNA 135.

Degradation of the PCR Products of DNA Fragments Located near one of the 5' Terminus and Near the 3' Termini As shown in FIG. 3, in order to obtain a part of single strand located near one of the 5' terminus of the PCR product 135 of DNA fragment purified by the above procedure, the PCR product 135 of DNA fragment is degraded at the strand located near the other 5' terminus and near the 3' termini, using an enzyme having an exonuclease activity. This procedure is performed to degrade the base sequence located near the adaptor introduced into one of the 5' terminus and obtain only a part of single strand located near the other 5' terminus used as a primer or as a template for the second amplification. In this embodiment, after the PCR product 135 of DNA fragment is reacted at 37° C. for 15 minutes using λ exonuclease ase 136, ethanol precipitation is performed for inactivation of the enzyme, purification and concentration. After reacting at 37° C. for 30 minutes using Klenow fragment 137, purification is carried out using a column QIA Quick Column (tradename, made by QUIAGEN Inc.) for the purposes of inactivation and removal of the enzyme, removal of the degraded oligonucleotides and purification and concentration of the reaction solution. By the foregoing procedures, a part of single strand located near one of the 5' terminus, which is shown by numeral 138 in FIG. 3, is obtained. In this embodiment, enzymes having a 5'→3' exonuclease activity and a 3'→5' exonuclease activity were employed to obtain a part of single strand located near one of the 5' terminus. However, in place of a 5'→3' exonuclease, a part of single strand located near one of the 5' terminus may also be obtained by inserting biotin into the 5' terminus required and purifying the DNA fragment with avidin-added magnetic beads.

Second Amplification Reaction

Figure 4:
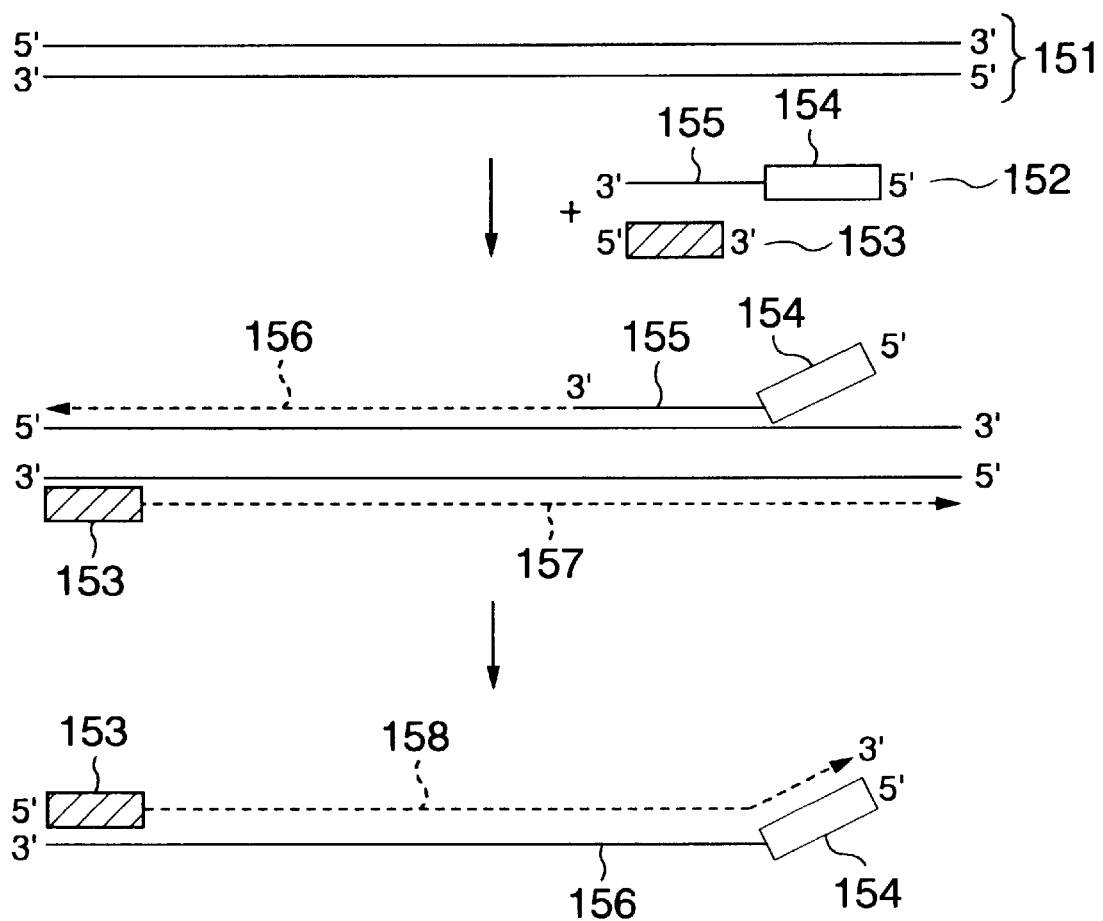
FIG. 4 is to explain the step for second amplification by PCR in an embodiment of the present invention.

FIG. 4 is to explain the step for second amplification by PCR. Using as a template sample DNA 151 before restriction enzyme digestion, second amplification is conducted using as primers single stranded DNA part 152 located near the 5' terminus and oligomer 153 having a part of sequence of the sample DNA. The oligomer has the same base sequence as primer (1) which is the base sequence of one of the 5' terminus in the intact sample DNA before enzymatic digestion. In a first reaction cycle, the single stranded DNA part 152 located near the 5' terminus is complementary to the template DNA only in a downstream base sequence part 155 of the adaptor base sequence 154 introduced at the 5' terminus thereof. The part 155 alone hybridizes with the template to proceed an extension reaction to the terminus of the template DNA, whereby the extension reaction product 156 is obtained. On the other hand, the oligomer 153 hybridizes to another strand of the template DNA to proceed its extension reaction, whereby the extension reaction product 157 is obtained. However, in the second and following reaction cycles, the extension reaction product 156 produced in the first cycle reaction can be used as a template in addition to the oligomer 153. Thus, an extension reaction further proceeds to obtain the extension reaction product 158. Upon PCR reaction, primers are added to the system in a large excess amount as compared to the amount of template DNA. The oligomer 153 that functions as a primer for the template and the single stranded DNA part 152 located near the 5' terminus are also added to the system in large excess amounts. For this reason, as the cycle proceeds, the oligomer 153 hybridizes more frequently to the extension reaction product 156, rather than to the template DNA. As a result, only the fragment between the oligomer 153 and the adaptor base sequence 154 is amplified by PCR.

Figure 5:
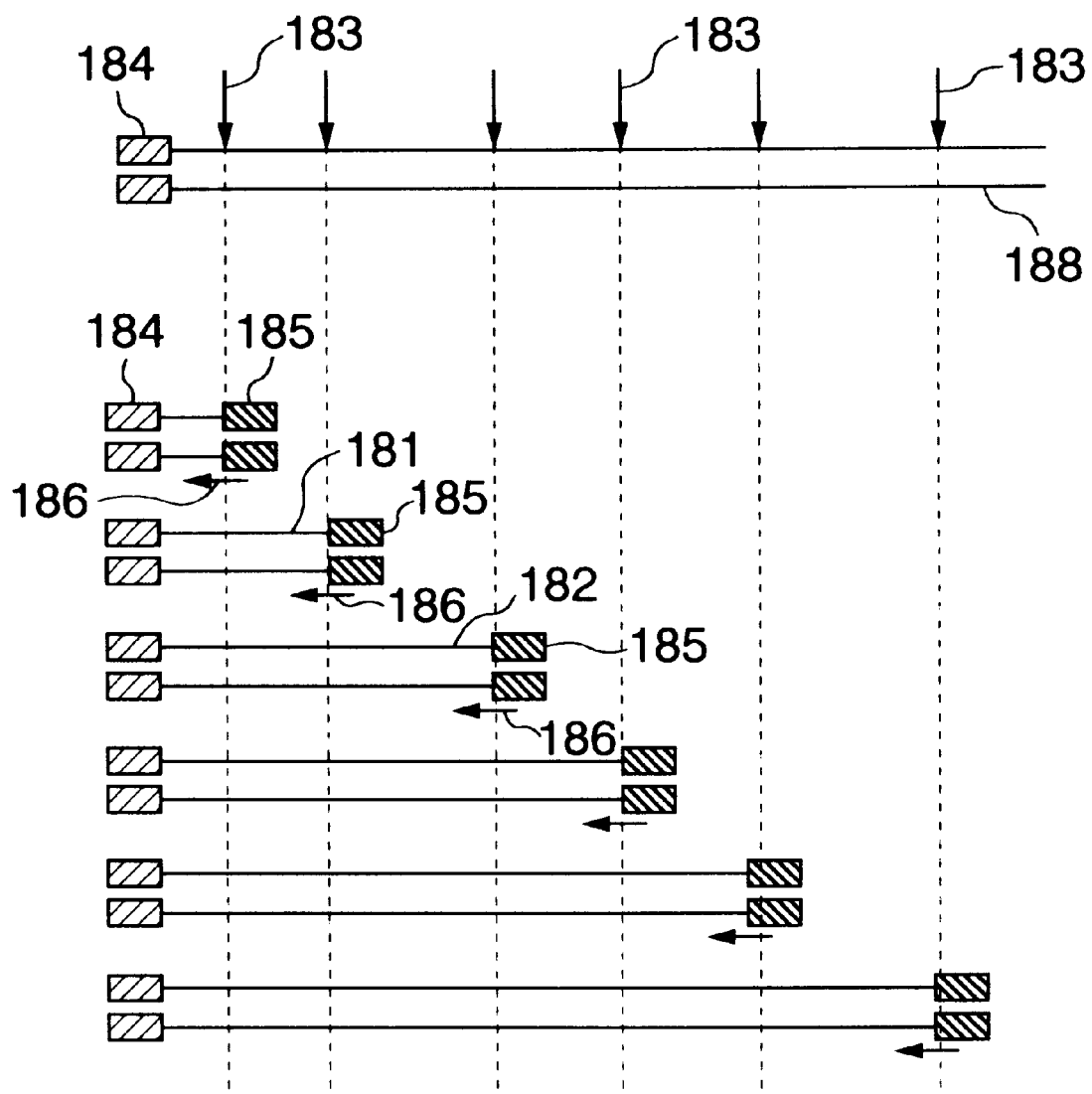
FIG. 5 shows the procedure for DNA sequencing of a sample DNA in an embodiment of the present invention, using a nested-deletion library.

FIG. 5 shows the procedure for DNA sequencing of a sample DNA, using a nested-deletion library. The sequences of DNA fragments 181 and 182 amplified by the second amplification above are determined at the restriction enzyme recognition sequence 183 of sample DNA 188. The start point 184 is all located at the same position and the other end point is determined at the restriction enzyme recognition sequence 183. The end point 185 contains a complementary base sequence to each selective primer for each fragment and sequencing is conducted using the end point 185 as a priming site. The arrow 186 shown in FIG. 5 indicates the sequencing direction. As described above, the sample library for nested-deletion is prepared and the full-length base sequence of sample DNA 188 before restriction enzyme digestion is determined by sequential DNA sequencing.

EXAMPLE 2

As a sample DNA, there is employed about 8.9 kbs human genome DNA inserted into a plasmid. In this embodiment, the steps of digesting the sample DNA with a restriction enzyme, introducing an oligomer having a known base sequence into the termini of each fragment, sequencing of two bases contiguous to the restriction enzyme recognition sequence of each DNA fragment, amplifying each DNA fragment by PCR and degrading a part of single strand located near one of the 5' terminus and near the 3' termini, of the PCR product of each DNA fragment are performed similarly to Example 1 shown in FIGS. 1 through 3.

Second Amplification

Figure 6:
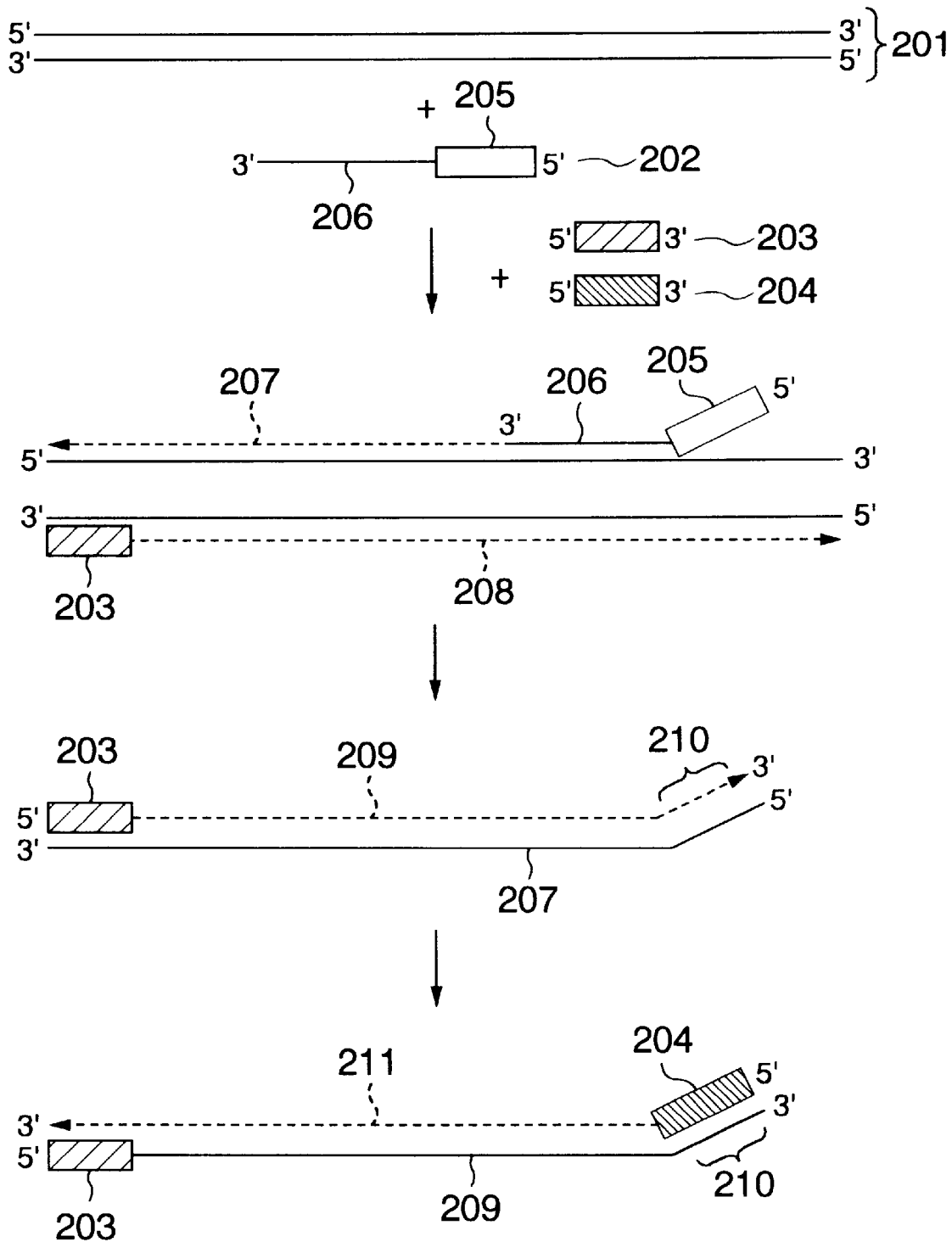
FIG. 6 is to explain the step for second amplification by PCR in an embodiment of the present invention, using a selective primer.

FIG. 6 is to explain the step for second amplification by PCR, using a selective primer. As shown in FIG. 6, using, as templates, sample DNA 201 before restriction enzyme digestion and the single stranded DNA part 202 located near the 5' terminus of DNA fragment, second amplification is conducted using as primers oligomer 203 having a part of sequences of the sample DNA before enzymatic digestion and the selective primer 132 used for PCR amplification of the DNA fragment in FIG. 3 (numeral 204 in FIG. 6). The oligomer 203 has the same base sequence as primer (1) which is the base sequence of one of the 5' terminus in the intact sample DNA before enzymatic digestion. In a first reaction cycle, the single stranded DNA part 202 located near the 5' terminus is complementary to the template DNA only in a downstream base sequence part 206 of the adaptor base sequence 205 introduced at the 5' terminus thereof, as shown in FIG. 6. The part 206 hybridizes with the template to proceed an extension reaction to the end of the template DNA, whereby the extension reaction product 207 is obtained. On the other hand, the oligomer 203 hybridizes to another strand of the template DNA to proceed its extension reaction, whereby the extension reaction product 208 is obtained. However, in the second and following reaction cycles, the extension reaction product 207 produced in the first cycle reaction can be used as a template in addition to the oligomer 203. Thus, an extension reaction further proceeds to obtain the extension reaction product 209. The product 209 produced in the second cycle reaction contains the base sequence of priming site 210 of the selective primer 204. Therefore, in the third and following reaction cycles, the selective primer 204 serves to proceed an extension reaction using the DNA strand of the product 209, whereby the extension reaction product 211 is obtained. Upon PCR reaction, primers are added to the system in a large excess amount, as compared to the amount of template DNA. The oligomer 203 that functions as a primer for the template and the selective primer 204 are also added to the system in large excess amounts. For this reason, as the cycle proceeds, the oligomer 203 hybridizes more frequently to the extension reaction product 207, rather than hybridizes to the template DNA. As a result, only the fragment between the oligomer 203 and the selective primer 204 is amplified by PCR.

Each DNA fragment amplified by the foregoing procedure is the same fragment as shown in FIG. 5 and thus, a sample library for nested-deletion can be prepared as shown in FIG. 5. The full-length base sequence of sample DNA 201 restriction enzyme digestion is thus determined by sequential DNA sequencing.

EXAMPLE 3

As a sample DNA, there is employed about 8.9 kbs human genome DNA inserted into a plasmid. In this embodiment, the steps of digesting the sample DNA with a restriction enzyme, introducing an oligomer having a known base sequence into the termini of each fragment, and sequencing of two bases contiguous to the restriction enzyme recognition sequence of each DNA fragment are performed similarly to Example 1 shown in FIGS. 1 and 2.

PCR Amplification of each DNA Fragment in the Mixture of DNA Fragments

Figure 7:
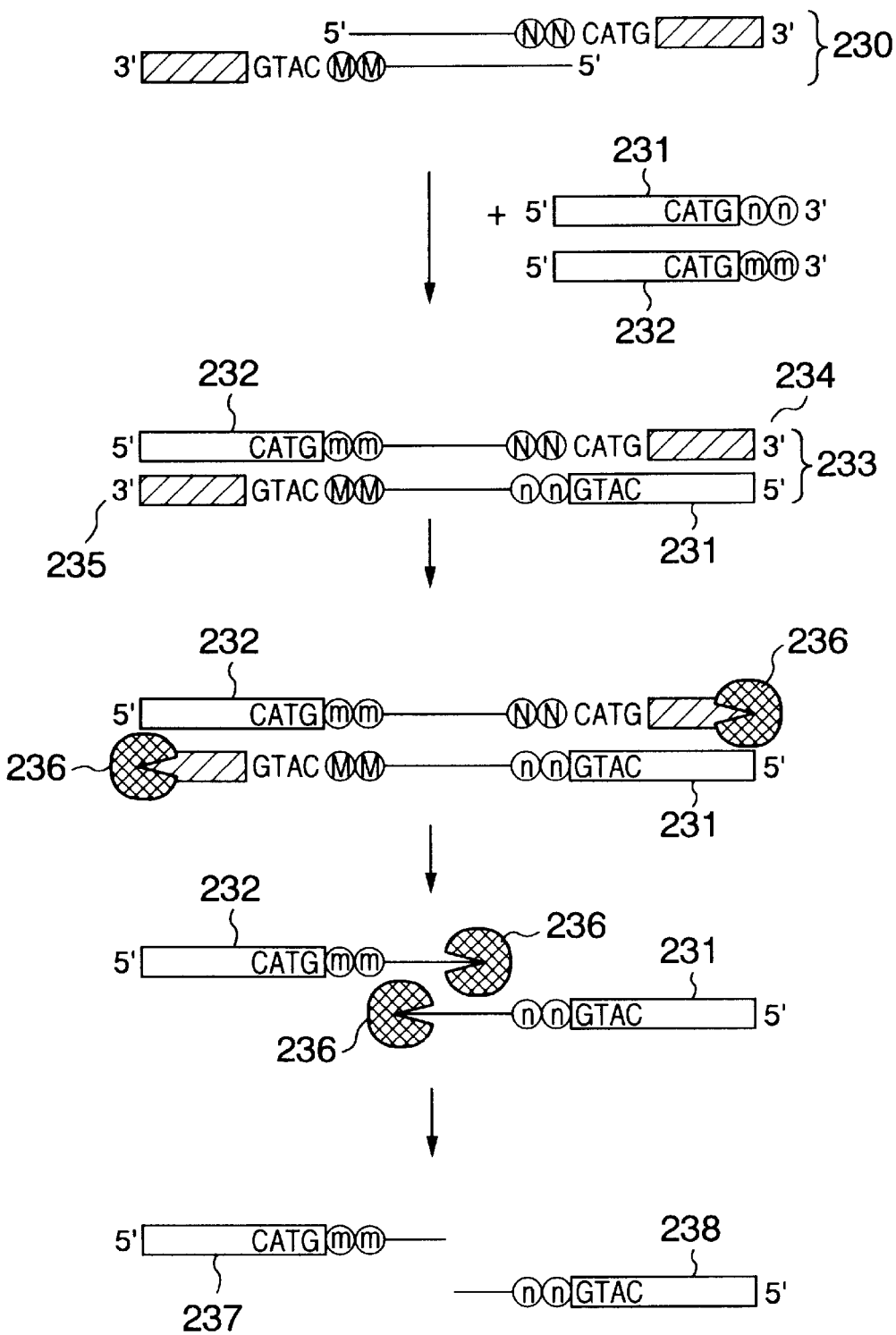
FIG. 7 is to explain, in an embodiment of the present invention, the steps of preparing a sample for nested-deletion library using a 3'→5' exonuclease.

FIG. 7 is to explain the steps of preparing a sample for nested-deletion library using a 3'→5' exonuclease. As shown in FIG. 7, each DNA fragment is amplified based on the sequencing information on the two bases contiguous to the restriction enzyme recognition sequences of the termini of each fragment determined as above. In FIG. 7, numeral 230 denotes a template DNA fragment. Based on the sequencing information of the terminal two bases determined above, one DNA fragment selected from the mixture is amplified by PCR, using a pair of selective primers 231 and 232 for each fragment. The DNA fragment amplified by PCR is purified and concentrated on a column QIA Quick Column (tradename, made by QUIAGEN Inc.) to remove the unreacted primers, dATP, dCTP, dGTP and dTTP. Hereinafter, the purified products are called PCR products of DNA fragments, which are made sample DNA 233.

Degradation of the PCR Products of DNA fragments Located Near the 3' Termini

As shown in FIG. 7, in order to obtain a part of single strand located near one of the 5' terminus of the PCR product 233 of DNA fragment purified by the above procedure, the PCR product 233 is degraded at the strand located near the 3' termini of the fragment, using an exonuclease enzyme. This procedure is performed to obtain one strand of the 5' terminus used as a primer or as a template for the second amplification. As shown in FIG. 7, after the PCR product 233 of DNA fragment is reacted at 37° C. for 15 minutes using exonuclease III 236, purification is carried out using a column QIA Quick Column (tradename, made by QUIAGEN Inc.) for the purposes of inactivation and removal of the enzyme, removal of the degraded oligonucleotides and purification and concentration of the reaction solution. By the foregoing procedures, the single strand DNA parts 237 and 238 located near the 5' terminus are obtained as shown in FIG. 7.

Second Amplification Reaction

Figure 8:
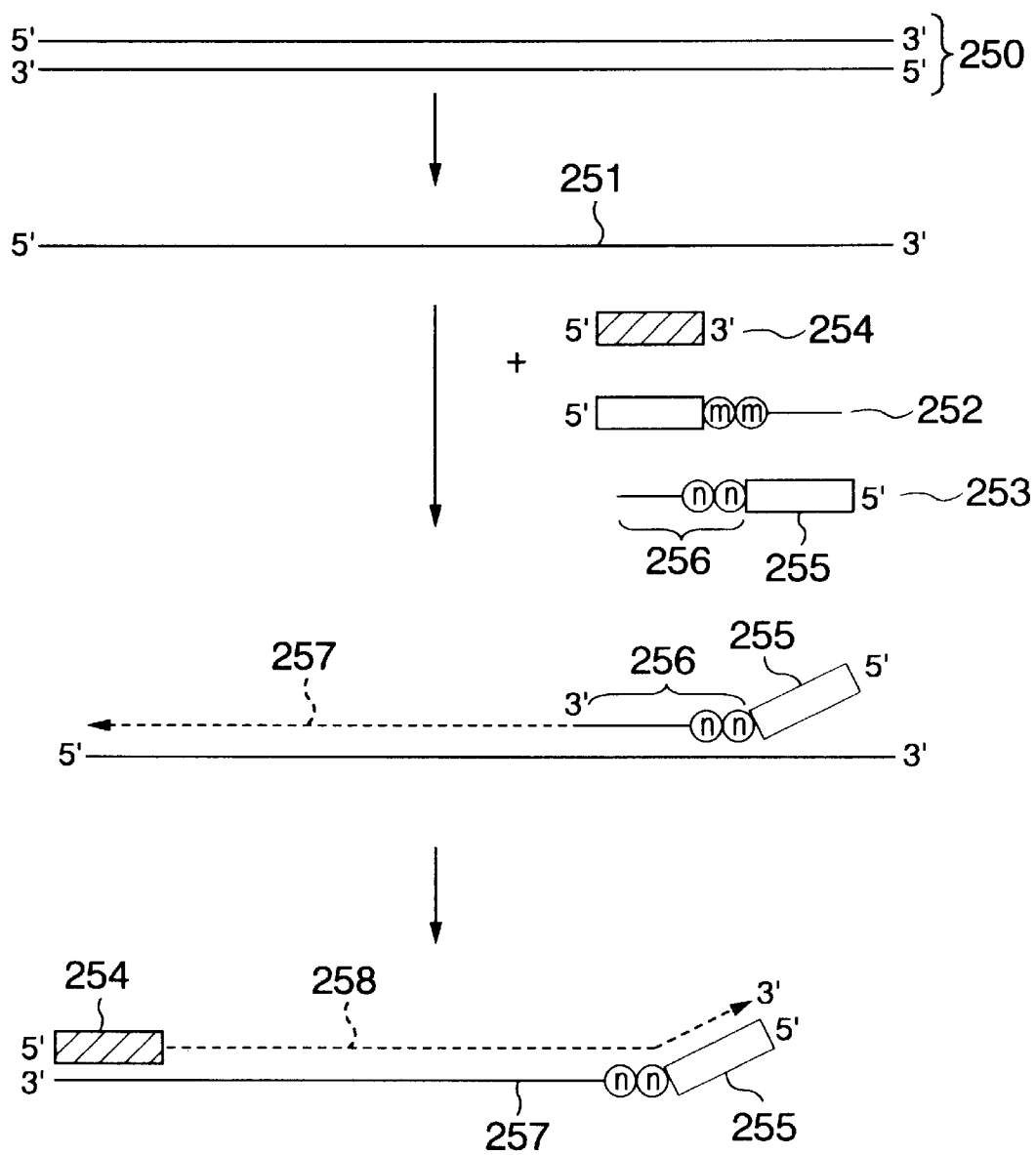
FIG. 8 is to explain the step for second amplification by PCR in an embodiment of the present invention.

FIG. 8 is to explain the step for second amplification by PCR. As shown in FIG. 8, a sample DNA 250 before restriction enzyme digestion is previously rendered a single strand and one strand only is recovered and purified. The sample DNA is amplified by PCR. In the PCR amplification, primers (1) and (2) described in Example 1 are employed and primer (1) alone is modified with biotin at the 5' terminus thereof. The thus amplified sample DNA is purified using avidin-added magnetic beads to recover only single strand 251 shown in FIG. 8. Using as a template the single stranded DNA 251, second amplification is conducted using as primers single stranded DNA 252 and 253 located near the 5' termini and oligomer 254 having a part of sequence of the intact sample DNA 251 before enzymatic digestion. The oligomer 254 has the same base sequence as primer (1) which is the base sequence of one of the 5' terminus of the single stranded DNA 251. In a first reaction cycle, the single stranded DNA part 256 located near the 5' terminus is complementary to the template DNA 251 only in a downstream base sequence part 256 of the adaptor base sequence 255 introduced at the 5' terminus of the single stranded DNA 251. The part 256 alone hybridizes with the template to proceed an extension reaction to the end of the template DNA, whereby the extension reaction product 257 is obtained. In the second reaction cycle, the oligomer 254 uses the extension reaction product 257 produced in the first cycle reaction as a template and thus, an extension reaction further proceeds to obtain the extension reaction product 258. As a result, the fragment between the oligomer 254 and the adaptor base sequence 255 is amplified by PCR.

Each DNA fragment amplified by the foregoing procedure is the same fragment as shown in FIG. 5 and thus, a sample library for nested-deletion can be prepared as shown in FIG. 5. The full-length base sequence of sample DNA 250 before restriction enzyme digestion is thus determined by sequential DNA sequencing.

EXAMPLE 4

As a sample DNA, there is employed about 8.9 kbs human genome DNA inserted into a plasmid. In this embodiment, the steps of digesting the sample DNA with a restriction enzyme, introducing an oligomer having a known base sequence into the termini of each fragment, sequencing of two bases contiguous to the restriction enzyme recognition sequence of each DNA fragment, amplifying each DNA fragment by PCR and degrading a part of the PCR product of each DNA fragment located near the 3' termini are performed similarly to Example 3 shown in FIGS. 1, 2 and 7.

Second Amplification

Figure 9:
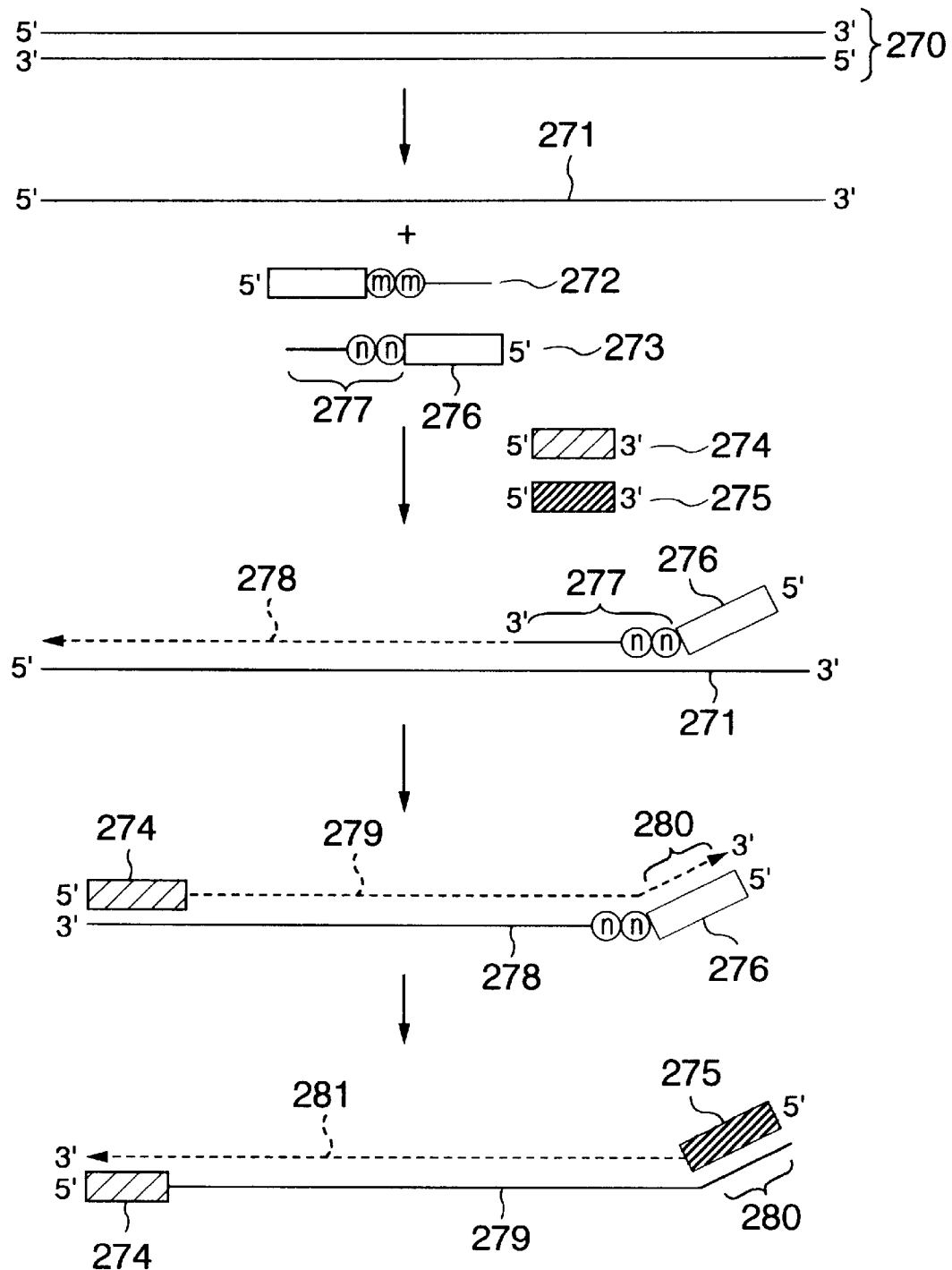
FIG. 9 is to explain the step for second amplification by PCR in an embodiment of the present invention, using a selective primer.

FIG. 9 is to explain the step for second amplification by PCR using a selective primer. As shown in FIG. 9, a sample DNA 270 before restriction enzyme digestion is previously rendered a single strand and one strand only is recovered and purified. The sample DNA is amplified by PCR. In the PCR amplification, primers (1) and (2) described in Example 1 are employed and primer (1) alone is modified with biotin at the 5' terminus thereof. The thus amplified sample DNA is purified using avidin-added magnetic beads to recover only single strand 271 shown in FIG. 9. Using as templates the single stranded DNA 271 and single stranded DNA 272 and 273 located near the 5' termini of the DNA fragment obtained above, second amplification is conducted using as primers oligomer 274 having a part of sequence of the single stranded DNA 271 and the selective primer 231 (275 in FIG. 9) used upon the PCR amplification of DNA fragment in FIG. 7. The oligomer 274 has the same base sequence as primer (1) which is the base sequence of the 5' terminus of the single stranded DNA 271. In a first reaction cycle, as shown in FIG. 9, only the downstream base sequence part 277 of the adaptor base sequence 276 introduced at the 5' terminus of the single stranded DNA 273 is complementary to the template DNA. The part 277 alone hybridizes with the template to proceed an extension reaction to the end of the template DNA, whereby the extension reaction product 278 is obtained. In the second reaction cycle, the oligomer 274 uses the extension reaction product 278 produced in the first cycle reaction as a template and thus, an extension reaction further proceeds to obtain the extension reaction product 279. The product 279 produced in the second cycle reaction contains the base sequence of priming site 280 of the selective primer 275. Therefore, in the third and following reaction cycles, the selective primer 275 serves to proceed an extension reaction using the DNA strand 279, whereby the extension reaction product 281 is obtained. As a result, only the fragment between the oligomer 274 and the selective primer 275 is amplified by PCR.

Each DNA fragment amplified by the foregoing procedure is the same fragment as shown in FIG. 5 and thus, a sample library for nested deletion can be prepared as shown in FIG. 5. The full-length base sequence of sample DNA 270 before restriction enzyme digestion is thus determined by sequential DNA sequencing.

EXAMPLE 5

As a sample DNA, there is employed about 8.9 kbs human genome DNA inserted into a plasmid. In this embodiment, the steps of digesting the sample DNA with a restriction enzyme, introducing an oligomer having a known base sequence into the termini of each fragment, and sequencing of two bases contiguous to the restriction enzyme recognition sequence of each DNA fragment are performed similarly to Example 1 shown in FIGS. 1 and 2.

PCR Amplification of each DNA Fragment in the Mixture of DNA Fragments

Figure 10:
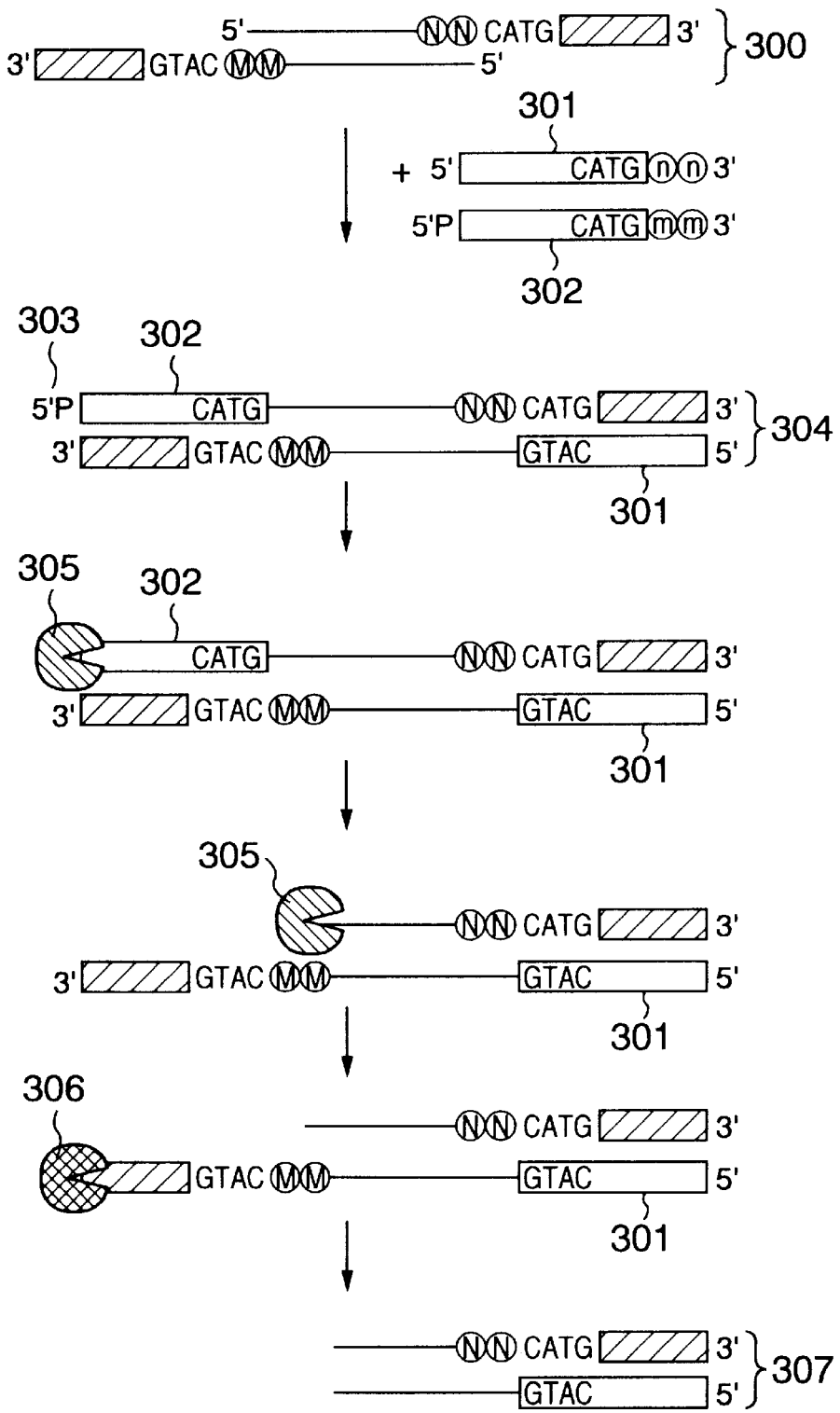
FIG. 10 is to explain the steps of preparing a sample for nested-deletion library in an embodiment of the present invention, using a 5'→3' exonuclease and a single strand degradation enzyme.

FIG. 10 is to explain the steps of preparing a sample for nested-deletion library, using a 5'→3' exonuclease and a single strand degradation enzyme. As shown in FIG. 10, each DNA fragment is amplified based on the sequencing information on the two bases contiguous to the restriction enzyme recognition sequences of the termini of each fragment determined by the foregoing procedures. Based on the sequencing information of the terminal two bases determined above, one DNA fragment selected from the mixture is amplified by PCR, using a pair of selective primers for each fragment. In FIG. 10, numeral 300 denotes a template DNA fragment. At this stage, one primer 302 out of paired two primers 301 and 302 used for the PCR reaction is modified and phosphorylated at the 5' terminus thereof. This modification is made to specifically degrade the phosphorylated 5' terminus 303 shown in FIG. 10, when one of the 5' terminus of the amplified DNA fragment is degraded in the following step. The DNA fragment amplified by PCR is purified and concentrated on a column QIA Quick Column (tradename, made by QUIAGEN Inc.) to remove the unreacted primers and dATP, dCTP, dGTP and dTTP. Hereinafter, the purified products are called PCR products of DNA fragments, which are made sample DNA 304.

Degradation of the PCR Products of DNA Fragments Located Near One of the 5' Terminus and the Single Stranded Part As shown in FIG. 10, in order to obtain a part of single strand located near one of the 5' terminus of the PCR product 304 of DNA fragment purified by the above procedure, the PCR product 304 of DNA fragment is degraded at the strand located near the other 5' terminus and near, using λ exonuclease and the single stranded DNA part is then degraded using S nuclease. This procedure is performed to obtain a part of single strand located near the other 5' terminus used as a primer or as a template for the second amplification. As shown in FIG. 10, after the purified PCR product 304 of DNA fragment is reacted at 37° C. for 15 minutes using λ exonuclease 305, ethanol precipitation is performed for inactivation of the enzyme, purification and concentration. After reacting at 37° C. for 30 minutes, using S nuclease 306, purification is carried out using a column QIA Quick Column (tradename, made by QUIAGEN Inc.) for the purposes of inactivation and removal of the enzyme, removal of the degraded oligonucleotides and purification and concentration of the reaction solution. By the foregoing procedures, double stranded DNA located near one of the 5' terminus, which is shown by numeral 307 in FIG. 10, is obtained.

Second Amplification

Figure 11:
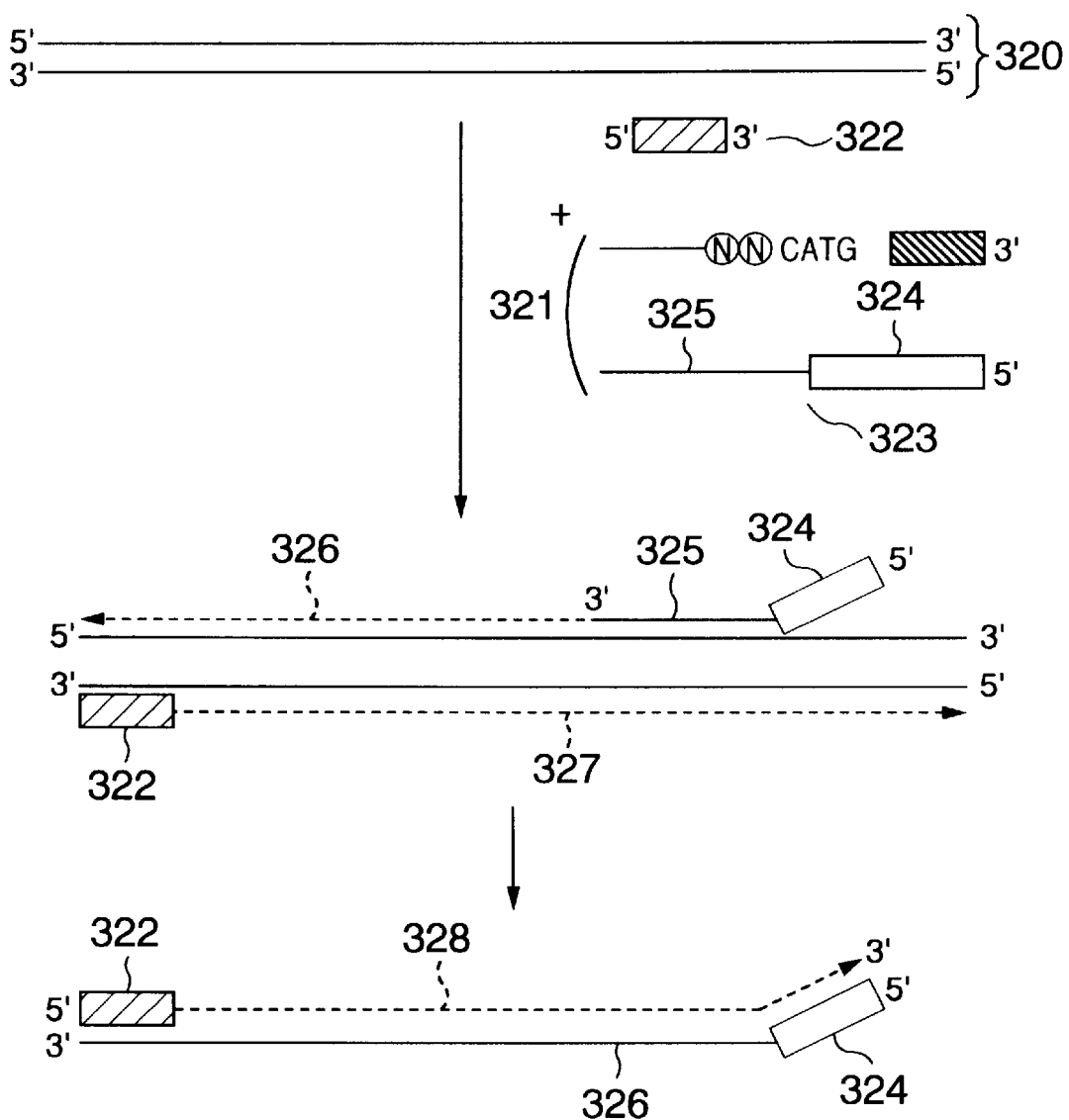
FIG. 11 is to explain the step for second amplification by PCR in an embodiment of the present invention.

FIG. 11 is to explain the step for second amplification by PCR. As shown in FIG. 11, using as a template sample DNA 320 before restriction enzyme digestion, second amplification is conducted using as primers double stranded DNA 321 located near the 5' termini of the DNA fragment obtained above and oligomer 322 having a part of sequence of the intact sample DNA 320 before enzymatic digestion. The oligomer 322 has the same base sequence as primer (1) which is the base sequence of one of the 5' terminus in the intact sample DNA before enzymatic digestion. In a first reaction cycle, as shown in FIG. 11, only the downstream base sequence part 325 of the adaptor base sequence 324 introduced at the 5' terminus of one strand 323 of the double stranded DNA 321 located near the 5' terminus of the DNA fragment is complementary to the template DNA. The part alone hybridizes with the template to proceed an extension reaction to the terminus of the template DNA, whereby the extension reaction product 326 is obtained. On the other hand, the oligomer 322 hybridizes to another strand of the template DNA to proceed its extension reaction, whereby the extension reaction product 327 is obtained. However, in the second and following reaction cycles, the extension reaction product 326 produced in the first cycle reaction also functions as a template. Thus, an extension reaction further proceeds to obtain the extension reaction product 328. Upon PCR reaction, primers are added to the system in a large excess amount as compared to the amount of template DNA. The oligomer 322 that functions as a primer for the template and the single stranded DNA part 323 located near the 5' terminus (double stranded DNA 321 located near the 5' terminus of the DNA fragment) are also added to the system in large excess amounts. For this reason, as the cycle proceeds, the oligomer 322 hybridizes more frequently to the extension reaction product 326, rather than to the template DNA. As a result, only the fragment between the oligomer 322 and the adaptor base sequence 324 is amplified by PCR.

Each DNA fragment amplified by the foregoing procedure is the same fragment as shown in FIG. 5 and thus, a sample library for nested deletion can be prepared as shown in FIG. 5. The full-length base sequence of sample DNA 320 before restriction enzyme digestion is thus determined by sequential DNA sequencing.

EXAMPLE 6

As a sample DNA, there is employed about 8.9 kbs human genome DNA inserted into a plasmid. In this embodiment, the steps of digesting the sample DNA with a restriction enzyme, introducing an oligomer having a known base sequence into the termini of each fragment, sequencing of two bases contiguous to the restriction enzyme recognition sequence of each DNA fragment, amplifying each DNA fragment by PCR and degrading a part of the PCR product of each DNA fragment located near the 5' terminus and single stranded part are performed similarly to Example 5 shown in FIGS. 1, 2 and 10.

Second Amplification

Figure 12:
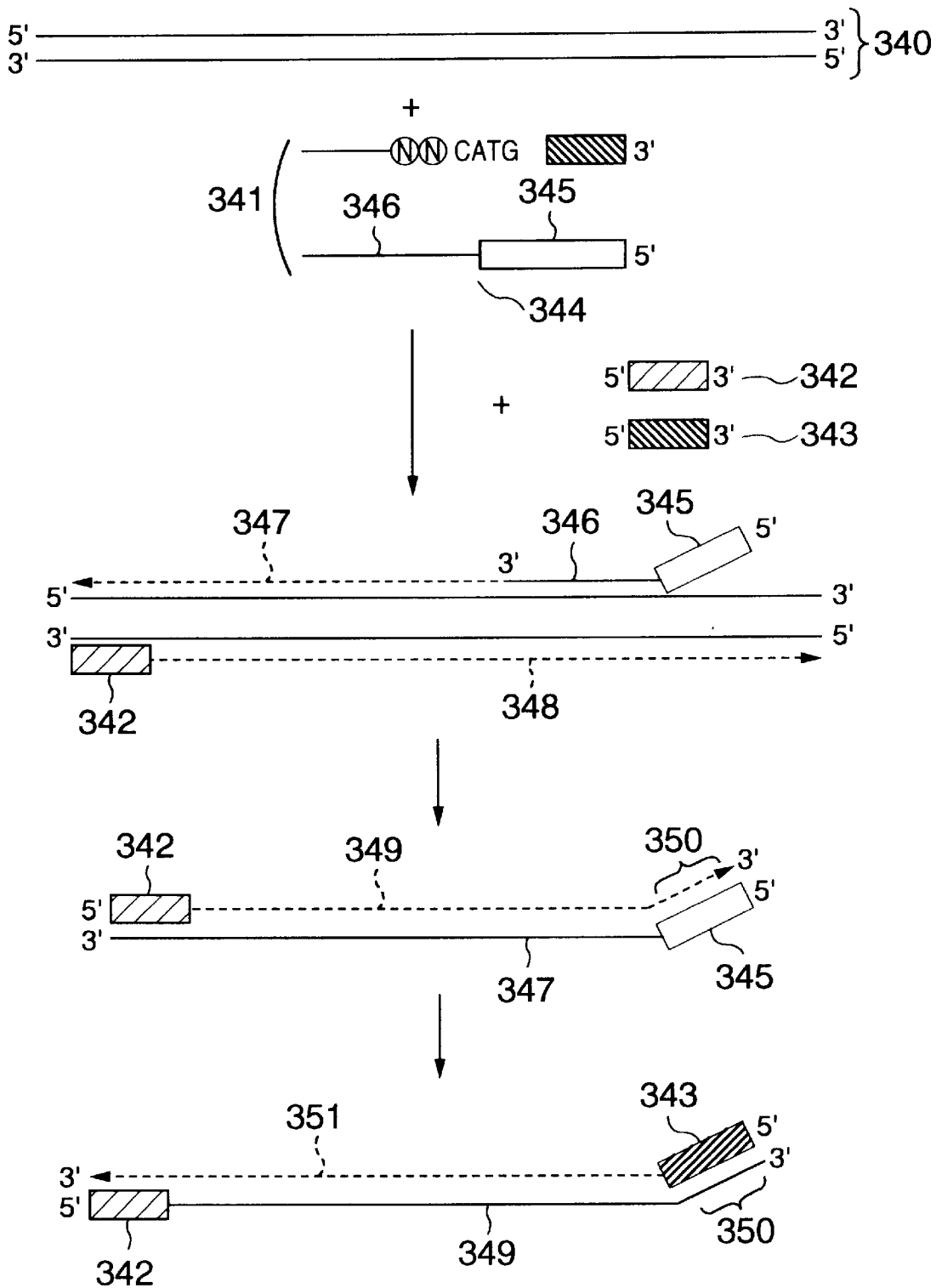
FIG. 12 is to explain the step for second amplification by PCR in an embodiment of the present invention, using a selective primer.

FIG. 12 is to explain the step for second amplification by PCR using a selective primer. As shown in FIG. 12, using, as templates, a sample DNA 340 before restriction enzyme digestion and a part 341 of double stranded DNA located near the 5' terminus of the DNA fragment obtained by the above procedures, second amplification is conducted by using as primers oligomer 342 having a part of sequences of the sample DNA before enzymatic digestion and the selective primer 301 used for PCR amplification of the DNA fragment in FIG. 10 (numeral 343 in FIG. 12). The oligomer 342 has the same base sequence as primer (1) which is the base sequence of one of the 5' terminus in the intact sample DNA before enzymatic digestion. In a first reaction cycle, the single strand part 344 of the double stranded DNA 341 located near the 5' terminus of the DNA fragment is complementary to the template DNA only in a downstream base sequence part 346 of the adaptor base sequence 345 introduced at the 5' terminus thereof, as shown in FIG. 12. The part 346 only hybridizes with the template to proceed an extension reaction to the end of the template DNA, whereby the extension reaction product 347 is obtained. On the other hand, the oligomer 342 hybridizes to another strand of the template DNA to proceed its extension reaction, whereby the extension reaction product 348 is obtained. However, in the second and following reaction cycles, the extension reaction product 347 produced in the first cycle reaction also functions as a template. Thus, an extension reaction further proceeds to obtain the extension reaction product 349. The product 349 produced in the second cycle reaction contains the base sequence of priming site 350 of the selective primer 343. Therefore, in the third and following reaction cycles, the selective primer 343 serves to proceed an extension reaction using the DNA strands 349 and 350 as templates, whereby the extension reaction product 351 is obtained. Upon PCR reaction, primers are added to the system in a large excess amount, as compared to the amount of template DNA. The oligomer 342 that functions as a primer for the template and the selective primer 343 are also added to the system in large excess amounts. For this reason, as the cycle proceeds, the oligomer 342 hybridizes more frequently to the extension reaction product 351, rather than hybridizes to the template DNA. As a result, the fragment between the oligomer 342 and the selective primer 343 is amplified by PCR.

Each DNA fragment amplified by the foregoing procedure is the same fragment as shown in FIG. 5 and thus, a sample library for nested deletion can be prepared as shown in FIG. 5. The full-length base sequence of sample DNA 340 before restriction enzyme digestion is thus determined by sequential DNA sequencing.

EXAMPLE 7

As a sample DNA, there is employed about 8.9 kbs human genome DNA inserted into a plasmid. In this embodiment, the steps of digesting the sample DNA with a restriction enzyme, introducing an oligomer having a known base sequence into the termini of each fragment, sequencing of two bases contiguous to the restriction enzyme recognition sequence of each DNA fragment, amplifying each DNA fragment by PCR and degrading a part of single strand located near one of the 5' terminus and near the 3' termini, of the PCR product of each DNA fragment are performed similarly to Example 1 shown in FIGS. 1 through 3.

Second Amplification

Figure 13:
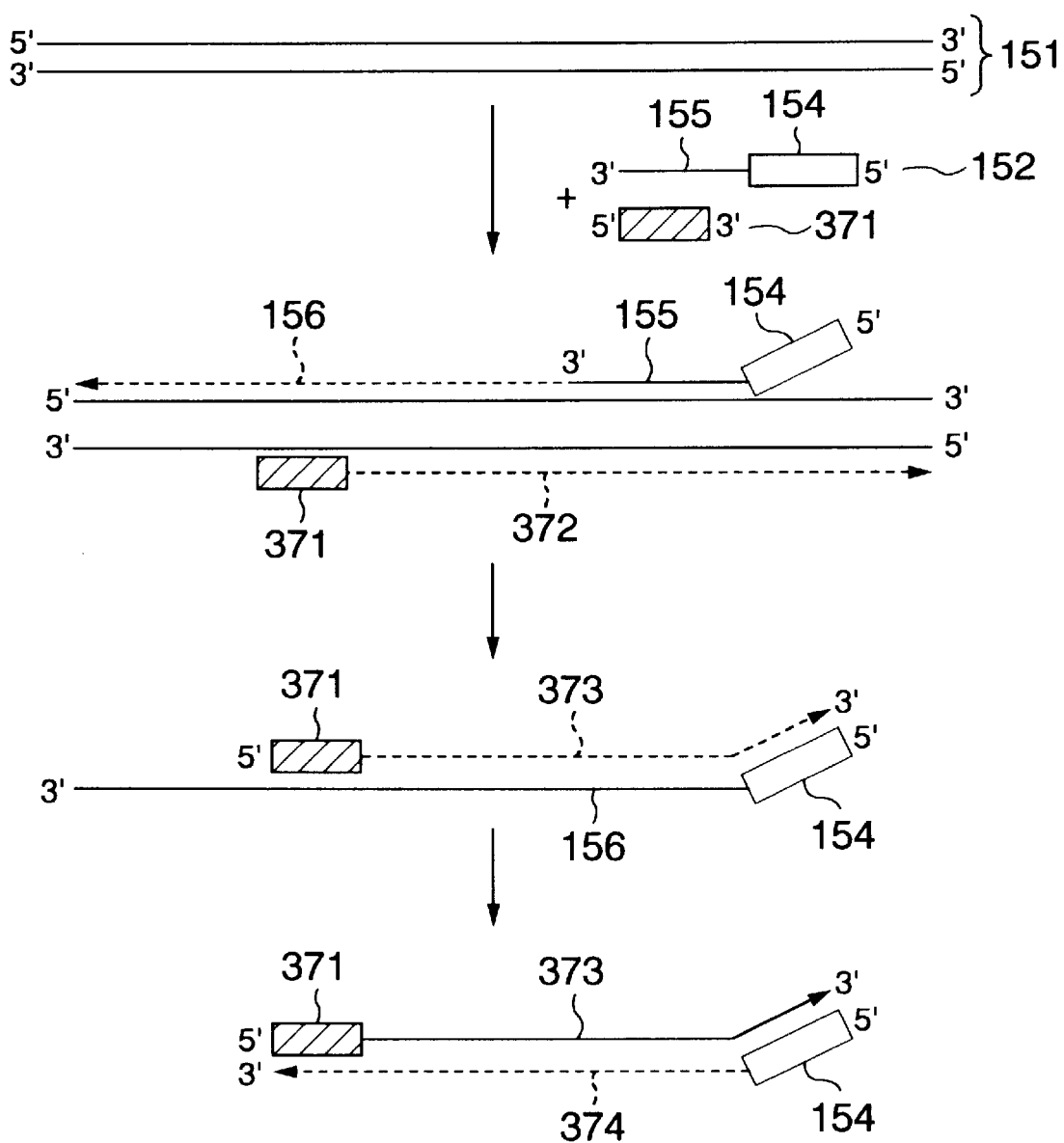
FIG. 13 is to explain the step for second amplification by PCR in an embodiment of the present invention, using a random primer.

FIG. 13 is to explain the step for second amplification by PCR, using an oligomer having a random base sequence (random primer). Using, as a template, sample DNA 151 before restriction enzyme digestion, second amplification is conducted by using as primers a single stranded DNA part 152 located near the 5' terminus of the DNA fragment obtained above and oligomer 371 having a random base sequence (random primer). The size of the random primer 371 is preferably 6 to 10 base pairs and its base sequence is arbitrary. In a first reaction cycle, the extension reaction product 156 shown in Example 1 and the extension reaction product 372 obtained from the site in which the random primer 371 hybridizes to the sample DNA are produced. In the second and following reaction cycles, the random primer 371 uses the extension reaction product 156 as a template. Thus, an extension reaction further proceeds to obtain the extension reaction product 373. The adaptor base sequence part 154 uses the extension reaction product 373 as a template to obtain the extension reaction product 374. As a result, only the fragment between the adaptor base sequence 154 and the random primer 371 is amplified in the cycle reactions.

What is claimed is:

1. A DNA sequencing method comprising:
   (1) obtaining a fragment by digesting a sample DNA and amplifying the fragment to obtain a first DNA fragment;
   (2) obtaining a second DNA fragment from said first DNA fragment, the second DNA fragment being able to hybridize with said sample DNA at least at the 3' terminus thereof; and
   (3) performing an extension reaction of complementary strand, using said sample DNA as a template to produce a third DNA fragment containing a base sequence complementary to said second DNA fragment and having a size longer than that of said second DNA fragment, and using the third DNA fragment as a template for sequencing of the sample DNA.

2. A DNA sequencing method according to claim 1, wherein said first DNA fragment is obtained by ligation of an oligomer having known base sequence after enzymatic digestion of said sample DNA and then amplification by PCR.

3. A DNA sequencing method according to claim 1, wherein said first DNA fragment is obtained by introducing poly A or poly U at the 3' terminus thereof by terminal deoxynucleotidyl transferase (TdT) and then subjecting to amplification by PCR.

4. A DNA sequencing method according to claim 1, wherein said first DNA fragment is prepared to be phosphorylated at one of the 5' termini and degraded using an enzyme having 5'→3' exonuclease activity and an enzyme having 3'→5' exonuclease activity thereby to obtain said second DNA fragment.

5. A DNA sequencing method according to claim 4, wherein said first enzyme is λ exonuclease and said second enzyme is any one selected from exonuclease III, BAL31 nuclease, Klenow fragment and T4 DNA polymerase.

6. A DNA sequencing method according to claim 1, wherein said first DNA fragment is degraded using an enzyme having a 3'→5' exonuclease activity and an oligomer introduced at the 3' terminus is removed thereby to obtain said second DNA fragment.

7. A DNA sequencing method according to claim 6, wherein said exonuclease III or BAL31 nuclease is employed as said enzyme having the 3'→5' exonuclease activity.

8. A DNA sequencing method according to claim 1, wherein said first DNA fragment is prepared to be phosphorylated at one of the 5' termini and degraded using an enzyme having a 5'→3' exonuclease activity and single stranded DNA part remaining after degradation is degraded by a single strand degradation enzyme to obtain said second DNA fragment.

9. A DNA sequencing method according to claim 8, wherein λ exonuclease is employed as said enzyme having the 5'→3' exonuclease activity and Mung Bean nuclease is employed as said single strand degradation enzyme.

10. A DNA sequencing method according to claim 1, wherein said sample DNA employed as the template is a double stranded DNA sample.

11. A DNA sequencing method according to claim 1, wherein said sample DNA employed as the template is a single stranded DNA sample.

12. A DNA sequencing method according to claim 1, wherein an oligomer having a base sequence complementary to a base sequence of the terminus of said sample DNA is used as a primer for use in PCR for obtaining said third DNA fragment.

13. A DNA sequencing method according to claim 1, wherein as a primer for use in PCR for obtaining said third DNA fragment, an oligomer having the same base sequence as said second DNA fragment or as a base sequence of the 5' terminus of said second DNA fragment is used.

14. A DNA sequencing method according to claim 1, wherein as a primer for use in PCR for obtaining said third DNA fragment, an oligomer having the same base sequence as said second DNA fragment or as a base sequence of the 5' terminus of said second DNA fragment and an oligomer having a random base sequence are used.

15. A DNA sequencing method according to claim 1, wherein as a primer for use in PCR for obtaining said first DNA fragment, an oligomer having a discrimination sequence comprising 1 to 3 bases at the 3' terminus thereof is used.

16. A reagents kit for use in a DNA sequencing method according to claim 1, comprising an enzyme for digesting said sample DNA and a primer for obtaining said first and third DNA fragments.

17. A reagents kit for use in a DNA sequencing method according to claim 1, comprising:
   an enzyme for digesting said sample DNA;
   an oligomer having a known base sequence;
   a reagent for introducing the oligomer having the known base sequence into the terminus of a digested DNA comprising a ligase or terminal deoxynucleotidyl transferase (TdT);
   a primer for use in an extension reaction;
   an enzyme having a 5'→3' exonuclease activity; and
   an enzyme having a 3'→5' exonuclease activity.

18. A reagents kit for use in a DNA sequencing method according to claim 1, comprising:
   an enzyme for digesting said sample DNA;
   an oligomer having a known base sequence;
   a reagent for introducing the oligomer having the known base sequence into the terminus of a digested DNA comprising a ligase or terminal deoxynucleotidyl transferase (TdT);
   a primer for use in an extension reaction; and
   an enzyme having a 3'→5' exonuclease activity.

19. A reagent kit for use in a DNA sequencing method according to claim 1, comprising:
   an enzyme for digesting said sample DNA;
   an oligomer having a known base sequence;
   a reagent for introducing the oligomer having the known base sequence into the terminus of a digested DNA comprising a ligase or terminal deoxynucleotidyl transferase (TdT);
   a primer for use in an extension reaction;
   an enzyme having a 5'→3' exonuclease activity; and
   a single strand degradation enzyme.

20. A DNA sequencing method comprising:
   (1) obtaining a fragment by digesting a sample DNA and amplifying the fragment to obtain a first DNA fragment;
   (2) obtaining a second DNA fragment from said first DNA fragment, the second DNA fragment being able to hybridize with said sample DNA at the 3' terminus thereof; and
   (3) performing an extension reaction of complementary strand, using said sample DNA as a template to produce a third DNA fragment containing a base sequence complementary to said second DNA fragment and having a size longer than that of said second DNA fragment, deleting a plurality of bases from one terminus of said sample DNA to obtain a group of deleted fragments, and using each of the deleted fragments as a template for sequencing of the sample DNA.

* * * * *